United States Patent
Oberhardt (12)

(10) Patent No.: US 6,251,615 B1
(45) Date of Patent: Jun. 26, 2001

(54) CELL ANALYSIS METHODS

(75) Inventor: Bruce J. Oberhardt, Raleigh, NC (US)

(73) Assignee: Cell Analytics, Inc., Durham, NC (US)

( * ) Notice: Subject to any disclaimer, the term of this patent is extended or adjusted under 35 U.S.C. 154(b) by 0 days.

(21) Appl. No.: 09/252,206

(22) Filed: Feb. 18, 1999

Related U.S. Application Data

(60) Provisional application No. 60/075,461, filed on Feb. 20, 1998, now abandoned.

(51) Int. Cl.[7] ............... G01N 33/567; G01N 33/557

(52) U.S. Cl. ............... 435/7.21; 435/7.2; 435/7.21; 435/7.92; 435/173.4; 435/287.1; 435/288.7; 435/971; 436/537; 436/34; 436/52; 436/63; 436/64; 436/165; 436/172; 436/807; 422/73; 422/82.05

(58) Field of Search ............... 422/55, 58, 61, 422/73, 82.05; 435/7.2, 7.1, 7.21–25, 287.1, 287.3, 7.92, 173.4, 173.5, 173.7, 287.6, 288.7, 326, 971, 973; 436/164, 524, 800, 807, 517, 518, 34, 52, 56, 63, 64, 147, 172, 537, 546; 356/39, 73, 315

(56) References Cited

U.S. PATENT DOCUMENTS

| | | | |
|---|---|---|---|
| 3,047,367 | 7/1962 | Keesler | 23/230 |
| 4,028,056 | 6/1977 | Snyder et al. | 23/230 |
| 4,100,797 | 7/1978 | Oberhardt et al. | 73/194 E |

(List continued on next page.)

FOREIGN PATENT DOCUMENTS

| | | | |
|---|---|---|---|
| 2423455 | 12/1974 | (DD) . | |
| 27 11 839 A1 | 9/1978 | (DE) | G01N/33/16 |
| 1598 129 | 9/1981 | (DE) | G01N/21/11 |
| 0 125 857 A2 | 11/1984 | (EP) | G01N/15/07 |
| 55-44914 | 3/1980 | (JP) | G01N/33/50 |
| 58-61447 | 4/1983 | (JP) | G01N/21/82 |
| 58-172537 | 10/1983 | (JP) | G01N/21/75 |
| WO 92/09878 | 6/1992 | (WO) . | |
| WO 97/12223 | 4/1997 | (WO) . | |

OTHER PUBLICATIONS

Marcus et al., Quantitative Analysis of Erythrocytes Containing Fetal Hemoglobin, Am J. Hematology 54:40–46, 1997.*

Megla, An Automatic White Blood Cell Analyzer, *SID Journal*, II(5):20–22 (Sep—Oct 74).

Halaby, Computer–Controlled Spectral Measurements of Blood Cells, *IEEE Transactions on Biomedical Engineering*, BME–26(1):34–43 (Jan. 79).

(List continued on next page.)

*Primary Examiner*—Long V. Le
*Assistant Examiner*—Gailene R. Gabel
(74) *Attorney, Agent, or Firm*—Myers Bigel Sibley & Sajovec, P.A.

(57) ABSTRACT

A method of analyzing cells in a carrier solution comprises the following steps: (a) Introducing the carrier solution into a conduit having a surface portion (preferably a substantially flat surface portion). The carrier solution has the cells suspended therein. (b) Allowing the cells to settle on the surface portion, the surface portion including at least one imaging field. In an alternate embodiment, one or more discreet capture zones (e.g., formed from an affinity species immobilized on the substrate or a textured region on the substrate) are formed on the surface portion, and this step (b) comprises capturing the cells in the capture zone. (c) Sequentially interrogating a plurality of the cells in the imaging field with emitted light. (d) Processing resultant light from the imaging field. (e) Generating digital information for each of the plurality of cells from the resultant light. (f) Generating a response file for each of the plurality of cells from the digital information. The response file generated in the method can be used for the sizing, enumeration, characterization, and/or classification of cells in the sample. Apparatus for carrying out the foregoing method is also disclosed, along with methods and apparatus employing reciprocal flow techniques.

31 Claims, 10 Drawing Sheets

U.S. PATENT DOCUMENTS

| | | | |
|---|---|---|---|
| 4,125,828 | 11/1978 | Resnick et al. | 340/146.3 |
| 4,300,906 | 11/1981 | Negersmith | 23/230 A |
| 4,520,108 | 5/1985 | Yoshida et al. | 436/52 |
| 4,610,544 | 9/1986 | Riley | 356/410 |
| 4,708,931 | 11/1987 | Christian | 435/7 |
| 4,876,504 | 10/1989 | Blake et al. | 324/204 |
| 4,931,384 | 6/1990 | Layton et al. | 435/7 |
| 5,215,926 | 6/1993 | Etchells, III et al. | 436/501 |
| 5,240,856 | 8/1993 | Goffe et al. | 435/299 |
| 5,260,192 * | 11/1993 | Russell et al. | 435/7.24 |
| 5,304,487 | 4/1994 | Wilding et al. | 435/291 |
| 5,312,757 | 5/1994 | Matsuyama et al. | 436/54 |
| 5,457,526 | 10/1995 | Kosaka | 356/72 |
| 5,464,752 | 11/1995 | Kortright et al. | 435/7.24 |
| 5,469,251 | 11/1995 | Kosaka et al. | 356/73 |
| 5,496,700 | 3/1996 | Ligler et al. | 435/7.1 |
| 5,523,238 | 6/1996 | Varon et al. | 436/69 |
| 5,538,855 | 7/1996 | Orfao de Matos Correira E. Vale | 435/724 |
| 5,548,395 | 8/1996 | Kosaka | 356/73 |
| 5,594,544 | 1/1997 | Horiuchi et al. | 356/73 |
| 5,644,388 | 7/1997 | Maekawa et al. | 356/73 |
| 5,952,184 | 9/1999 | Shaw et al. | 435/7.21 |

OTHER PUBLICATIONS

Eisert et al.; Simple Flow Microphotometer for Rapid Cell Population Analysis, *Rev. Sci. Instrum.*, 46(8):1021–1024 (Aug. 75).

V.E. Cosslett; Chapter 6—Flying–Spot Microscopes, *Modern Microscopy or Seeing the Very Small*, pp. 128–133, Cornell Paperbacks, Cornell University Press, Ithaca, New York (1966).

Horvath et al.; Measurement of Radial Transport in Slug Flow Using Enzyme Tubes, *Ind. Eng. Chem. Fundam.*, 12(4):431–439 (1973).

Provisional Patent Application entitled Cell Analysis Methods and Apparatus, 53 pages, Feb. 20, 1998.

PCT International Search Report for Int'l Appl'n No. PCT/US 99/03476, dated Aug. 5, 1999.

* cited by examiner

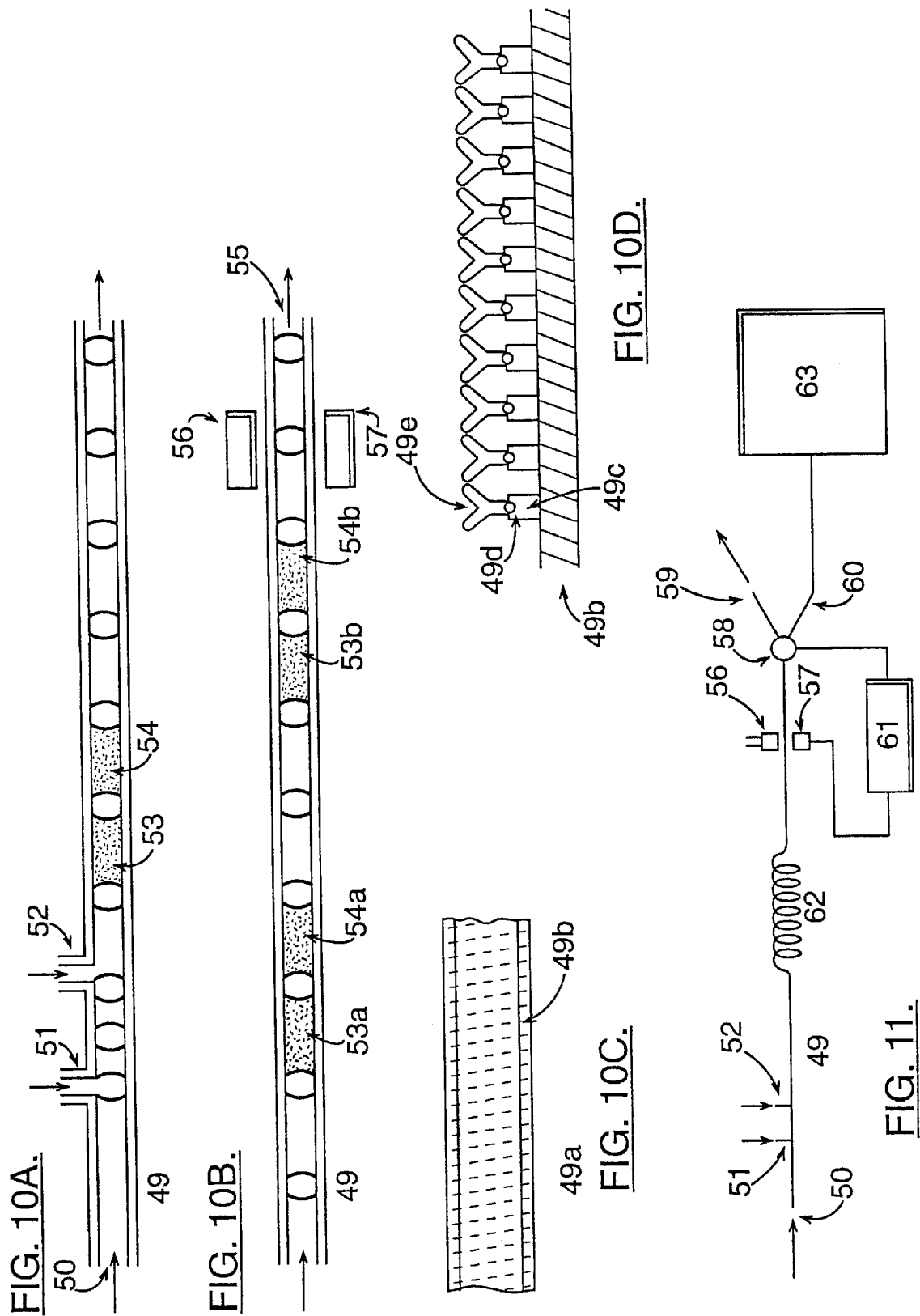

CELL ANALYSIS METHODS

This application claims priority from U.S. Provisional Application Ser. No. 60/075,451, filed Feb. 20, 1998, now abandoned the disclosure of which is incorporated by reference herein in its entirety.

FIELD OF THE INVENTION

The present invention relates to methods and apparatus for analyzing cells, and particularly relates to methods and apparatus for analyzing cells suspended in a carrier solution.

BACKGROUND OF THE INVENTION

The identification and characterization of cells are important procedures in biology and medicine. Cells are the basic units of life and are deceptively complicated. Some cells remain attached to an extracellular matrix and thus form part of a larger structure. Other cells are free to move about. Examples of the former are structural cells of green plants and mammalian nerve cells and bone cells. Examples of the latter are bacteria, protozoa, and mammalian blood cells. Some cells are normally attached to extracellular matrices but may be freed by mechanical or enzymatic (proteolytic) disruption and studied, for example cells of the liver (hepatocytes).

Automated liquid flow systems have been used to analyze cells. These systems have found particular application for blood cell analysis in the form of cell counters, hematology analyzers, and flow cytometry systems. Cell counters provide counts of and size of cells in suspension. Hematology analyzers may go further by providing counts on major subsets of white blood cells, such as granulocytes and/or lymphocytes, platelets, and on subsets of red blood cells. Hematology analyzers also measure hemoglobin and additional parameters derived from these basic measured parameters or combinations of these parameters. Flow cytometry systems measure normal and abnormal cells and find application in tracking patients with abnormal cells. Flow cytometers are used in research, and more expensive versions are equipped with cell sorting capability. Flow cytometers are open ended systems requiring significant sample preparation by a trained operator. Hematology analyzers are typically dedicated flow cytometers with automated sample preparation, designed for high volume (large workload) analysis.

One of the disadvantages of flow cytometry systems is that a tiny fraction of cells that are abnormal may not be resolved from a larger population. Another disadvantage is that it is not possible to examine cells after characterization, because the cells have been lost to a waste container. To overcome this latter limitation, cell sorting systems were developed. These flow cytometry systems can direct cells that meet preset criteria to collection containers. These systems, however, are generally very expensive. Moreover, they require a priori knowledge of the cell population characteristics, which is sometimes not available. Another type of cell analysis system has been designed that prepares a blood smear and stains it for each sample so that subsequent microscopic analysis with manual examination is possible. Slide makers and slide stainers can also be separate machines. There are also automated instruments that characterize the images obtained from stained blood smears and other stained smears containing cells. These instruments are sometimes called pattern recognition machines. Generally, pattern recognition systems fail to duplicate the ability of a human technologist to discriminate between normal and abnormal cells and differentiate between different types of cells. Often they are subject to discrimination errors due to variability in staining.

Another disadvantage of flow cytometers and pattern recognition machines is that it is generally difficult and inconvenient to remove the genetic material of cells that have been characterized for further analysis (e.g., sequencing). In addition, flow cytometry systems must generally be periodically cleaned and decontaminated from exposure to hazardous biological materials. Furthermore, when cell populations are measured with automated systems, thresholds must usually be set using calibration standards and controls. Typically, this is achieved with uniformly-sized particles and cell samples that simulate the cells. The calibration procedure requires additional time and is performed on the instrument by a trained operator. Accordingly, flow cytometry instruments are expensive and labor intensive. They are usable by highly trained laboratory professionals, only. Accordingly, there remains a need for a system that can be used for the simple and convenient analysis of cells in solution.

SUMMARY OF THE INVENTION

The present invention enables convenient analysis of samples containing suspended cells for research and/or clinical use. In one embodiment, this analysis involves the capture of or delay in transit time of cells with specific surface molecules by means of affinity interactions with test surfaces. The operation of a cell analysis system according to this invention is simple, yet the number of parameters that may be measured is substantially increased over what may be achieved by conventional cell analysis systems.

One object of this invention is to provide methods and apparatus that may be used when it is desired to measure the kinetics of cell capture by test surfaces containing designated affinity molecules (receptors or ligands, antibodies or antigens) to provide a new analytical tool for research and clinical applications. With this invention, the kinetics of cell capture can be determined as a function of convective effects, such as shear forces acting on the cell, and temperature. Temperature affects cell membrane fluidity and influences bond formation with affinity molecules such as antibodies. The kinetics of dissociation of captured cells under the influence of shear forces and temperature may also be determined.

Another object is to provide a system that may be used for analyzing cell attachment to surfaces with affinity molecules by precise flow control, where this flow control may be open loop control via any of a variety of computer programs for flow rate versus time or may be closed loop control using feedback to the computer from sensors that measure cell capture events.

It is another object of this invention to provide a system that may be used for measuring a variety of different types of cells.

Another object of this invention is to provide a cell analysis system that may be used to retain cells for further analysis. This further analysis can be microscopic, genetic, or molecular in nature.

Another object is to permit cell standards and controls to be incorporated, as part of the analytical procedure, in self-contained analysis cartridges, obviating extra steps and providing a system that is usable by individuals without laboratory training.

Another object of this invention is to provide a system that may be used for functional analysis of cell interaction with surfaces containing affinity molecules, thus simulating biological functions of cell adherence to extracellular surfaces and to surfaces of other cells, and eventually measuring cell metabolic changes, such as degranulation, shape changes, and secretion of cell products.

It is a further object to provide a system that may be used for functional analysis of cells by providing surfaces that can capture cells and activate other cell functions such as cell spreading across the surface and the appearance on the cell surface of new receptors.

Yet another object of this invention is to provide a potentially convenient methodology and apparatus for researchers to affix unique affinity molecules, such as specific antibody, to surfaces contained therein so that a sample containing cells may be conveniently analyzed.

A further object is to provide a clinical cell analysis system that may be embodied so as to require minimal operator steps and can perform tests and can perform data management and data transmission functions.

Yet another object is the provision of a system that may be used to analyze all major blood cell types with a minimum of reagent additions and without requiring lysis of red blood cells in order to make measurements of other cell types.

A first aspect of the present invention is a method of analyzing cells in a carrier solution. The method comprises:

(a) introducing the carrier solution into a conduit having a surface portion, the carrier solution having the cells suspended therein (e.g., by flowing the solution into the conduit with a pump, by capillary action, etc.);

(b) contacting the cells to the surface portion, the surface portion containing at least one imaging field;

(c) sequentially interrogating a plurality of the cells in the imaging field with at least two different types of emitted light;

(d) processing resultant light from the imaging field for each of the at least two different types of emitted light;

(e) generating digital information for each of the plurality of cells from the resultant light for each of the at least two different types of emitted light; and then (f) generating a response file for each of the plurality of cells from the digital information for each of the at least two different types of emitted light.

The introducing step may be carried out by any suitable means, such as capillary action, but is preferably carried out by flowing the solution through the conduit. The contacting step may be carried out by allowing the cells to settle on the surface portion. Or the the surface portion may be provided with a discreet capture zone formed thereon, with the capture zone positioned in the imaging field, and with the contacting step carried out by binding the cells to the capture zone.

A second aspect of the present invention is a method of preparing cells in a solution for detection, the method comprising:

(a) flowing (e.g., in a differential flowing step as discussed below) the cells in the solution through a conduit having a surface portion, the surface portion having a discreet capture zone formed thereon;

(b) capturing the cells in the capture zone, the capture zone including at least one imaging field; and then (c) staining the cells in the capture zone.

The staining step may be followed by the step of:

(d) washing the cells to remove excess stain.

The staining step, and the washing step if present, may be followed by the step of:

(e) detecting the stained cells in the imaging field.

The detecting step may comprise the steps of:

(f) interrogating a plurality of the cells in the imaging field with emitted light;

(g) processing resultant light from the imaging field;

(h) generating digital information from the resultant light for each of the cells; and (i) generating a response file for each of the plurality of cells.

The interrogating step may be a sequentially interrogating step carried out with different types of emitted light, as described above.

The foregoing methods may be practiced in a variety of ways. The at least two different types of emitted light may differ in a property such as frequency, intensity, direction of travel with respect to the cells, or combinations thereof. The resultant light may be light reflected by, absorbed by, scattered by, transmitted through, generated by molecules associated with the cells, and generated by molecules displaced by the cells. The carrier solution may comprise a biological fluid (which may be diluted with buffer or other reagent solution prior to use) or may be a buffered sample medium. Typically, the surface portion is a substantially flat surface portion. The processing step typically comprises an optical detection step followed by an electronic processing step. Typically, the contacting step is carried out by staining the cells, as noted above.

An advantage of the present invention is the variety of different information that can be stored in the response files for subsequent use. The response files may include the location and boundaries of each of the plurality of cells. A histogram plot of parameters for the plurality of cells can be generated from the response files. A cell scatter or cell distribution diagram from the response files. With the response files generated (depending of course of the particular information stored) one can proceed to: determine viability for each of the plurality of cells from the response files; determine the proliferation index of the plurality of cells from the response files; determine the incidence of apoptosis of the cells from the response files; count the cells from the response files; determining the DNA content of the cells from the response files; detect specific cytoplasmic or cell surface markers from the response files; determine the activation state of the cells from the response files; classify the plurality of cells according to type from the response files. A particular advantage of the present invention is that live cells can be used, as opposed to only dead cells.

Where capture zones are employed in the methods above, the surface portion may have at least one additional different capture zone formed thereon to provide a plurality of different discreet capture zones (e.g., 2 or 3 to 6 or 10), each having an imaging field; and the sequentially interrogating step may be repeated for each of the imaging fields in each of the capture zones. Different cell types may be bound in each of the different capture zones.

Various manipulations can be carried out with the carrier solution flow to enrich or optimize the binding or settling of the cells, or gain additional information about the cells. For example, the flow of the cells in the solution during the contacting step may be modified by feedback from by the resultant light or the response files. The sequentially interrogating step may be followed by the steps of: altering the rate of flow of the solution through the conduit; and then repeating the sequentially interrogating step. The sequentially interrogating step is followed by the steps of: altering the temperature of the cells in the capture zone; and then repeating the sequentially interrogating step.

Cells in the imaging field, particularly cells bound in capture zones (particularly capture zones that comprise an affinity species immobilized thereon or a textured segment formed thereon), may be further manipulated, particularly after they have been interrogated. One may proceed by lysing cells bound to the capture zone, and analyzing (e.g., sequencing) nucleic acid released from the lysed cells. One may transiently permeabilize the cells to release a portion of the contents thereof, while retaining nucleic acid for subsequent analysis therein. One may proceed by permeabilizing cells bound to the capture zone to induce leakage of contents thereof or permit the introduction of dyes therein. One may proceed by lysing cells bound to the capture zone to form cell ghosts.

A third aspect of the present invention is an apparatus for analyzing cells in a solution. The apparatus comprises:

(a) a conduit having a surface portion;

(b) means such as a pump for flowing the solution through the conduit so that the cells contact the surface portion, the surface portion containing at least one imaging field;

(c) means such as light sources and/or filters for sequentially interrogating a plurality of the cells in the imaging field with different types of emitted light;

(d) means such as a light detector (e.g., a camera such as a CCD camera) for processing resultant light from the imaging field for each of the different types of emitted light;

(e) means such as an electronic circuit or processor for generating digital information from the resultant light for each of the cells for each of the different types of emitted light; and (f) means such as a software program running in a general purposes computer, or other hardware and/or software systems, for generating a response file for each of the plurality of cells from each of the different types of emitted light.

The surface portion may include a capture zone as described above. The surface portion may have at least one additional different capture zone formed thereon to provide a plurality of different discreet capture zones, each having at least one imaging field; and wherein the means for sequentially interrogating includes means for repeating the sequential interrogation for each of the imaging fields in each of the capture zones.

A fourth aspect of the present invention is an apparatus for analyzing cells in a solution, the apparatus comprising:

(a) means such as a cartridge holder and/or a movable stage for positioning cells to be analyzed in an imaging field;

(b) means such as light sources and/or filters for sequentially for sequentially interrogating a plurality of the cells in the imaging field with different types of emitted light; the means for sequentially interrogating including at least two different sources of emitted light;

(c) means such as a light detector (e.g., a camera such as a CCD camera) for processing resultant light from the imaging field for each of the different types of emitted light;

(d) means such as an electronic circuit or processor for generating digital information from the resultant light for each of the cells for each of the different types of emitted light; and (e) means such as a software program running in a general purposes computer, or other hardware and/or software systems, for generating a response file for each of the plurality of cells from each of the different types of emitted light.

A fifth aspect of the invention is cell analysis cartridge useful for analyzing cells in a carrier solution, the cartridge comprising:

(a) a substantially flat planar body member having a top portion, a bottom portion, and an elongate fluid channel formed therein;

(b) at least two openings formed in the body member and in fluid communication with the fluid channel;

(c) a substantially optically transparent, non-distorting window formed on one of the top or bottom portions, the window forming an internal surface portion of the elongate fluid channel;

(d) the internal surface portion including at least one imaging field; and (e) the imaging field having a cell binding layer formed thereon.

Preferably, a substantially optically transparent window is formed on the other of the top or bottom portions. The binding layer may be a nonspecific or specific binding layer, and may be a layer of capture species immobilized or bound to the internal surface portion. The cartridge could be used in an apparatus as described herein, on a conventional microscope, etc.

A further aspect of the present invention is a cell capture method useful for the enrichment or analysis of cells in a solution, the method comprising:

(a) differentially flowing the cells in the solution through a conduit having a surface portion, the surface portion having a discreet capture zone formed thereon; while (b) capturing the cells in the capture zone.

Captured cells can then be examined with a method and apparatus as described above, on a conventional microscope, etc.

The differentially flowing step may comprise a reciprocally flowing step, or may comprise the step of increasing the rate of flow of the solution through the conduit so that a first group of weakly bound cells is removed from the capture zone and a second group of strongly bound cells remains in the capture zone (thereby permitting two different cell populations to be separated, or the immobilized cells to be probed based upon their binding affinity to the capture zone). Typically, the capture zone comprises an affinity species immobilized on the surface portion, a textured segment of the surface portion, a fenestrated capture zone, or any other suitable capture technique, system or means.

A further aspect of the present invention is a cell capture apparatus useful for the enrichment or analysis of cells in a solution, the apparatus comprising:

(a) a conduit having a surface portion, the surface portion having a discreet capture zone formed thereon;

(b) supply means such as a pump (particularly a syringe pump) for supplying the solution to the conduit; and (c) differential flow means such as a pump controller or control circuit (which may be a hardware, software, or both hardware and software controller) for differentially flowing the cells in the solution through the conduit (e.g., reciprocally flowing the solution through the conduit, or increasing the rate of flow of the solution through the conduit so that a first group of weakly bound cells is removed from the capture zone and a second group of strongly bound cells remains in the capture zone.).

Again, the capture zone may comprise an affinity species immobilized on the surface portion, may comprise a textured segment of the surface portion, a fenestrated capture zone, or any other suitable capture technique, system or means. The apparatus could be implemented in an apparatus as described above, in a conventional microscope, etc.

The foregoing and additional objects and aspects of the present invention are explained in detail in the drawings herein and the specification below, in which:

BRIEF DESCRIPTION OF THE DRAWINGS

FIG. 6A schematically illustrates a capture zone of the invention with reporter species bound thereto;

FIG. 6B illustrates a capture zone of the invention with reporter species displaced by a single bound cell;

FIG. 6C illustrates a capture zone of the invention with reporter species displaced by a plurality of bound cells;

FIG. 7A illustrates a capture zone of the present invention free of reporter species;

FIG. 7B illustrates a capture zone of the invention with cells bound thereto;

FIG. 7C illustrates a capture zone of the invention with cells bound thereto and an affinity species to be detected bound to the cells;

FIG. 10A illustrates a conduit of the invention in which flow of cells is retarded by a capture zone, in this case using a segmented continuous flow (or discontinuous flow) system;

FIG. 10B is a downstream illustration of the conduit of FIG. 10A illustrating a light source and photodetector;

FIG. 10C is a detailed view of FIG. 10B showing a capture zone therein;

FIG. 10D is a detailed view of a portion of FIG. 10C showing the structure of the capture zone;

FIG. 11 schematically illustrates an apparatus employing the conduit of FIGS. 10A and B;

DETAILED DESCRIPTION OF THE PREFERRED EMBODIMENTS

1. Definitions

Figure 1:
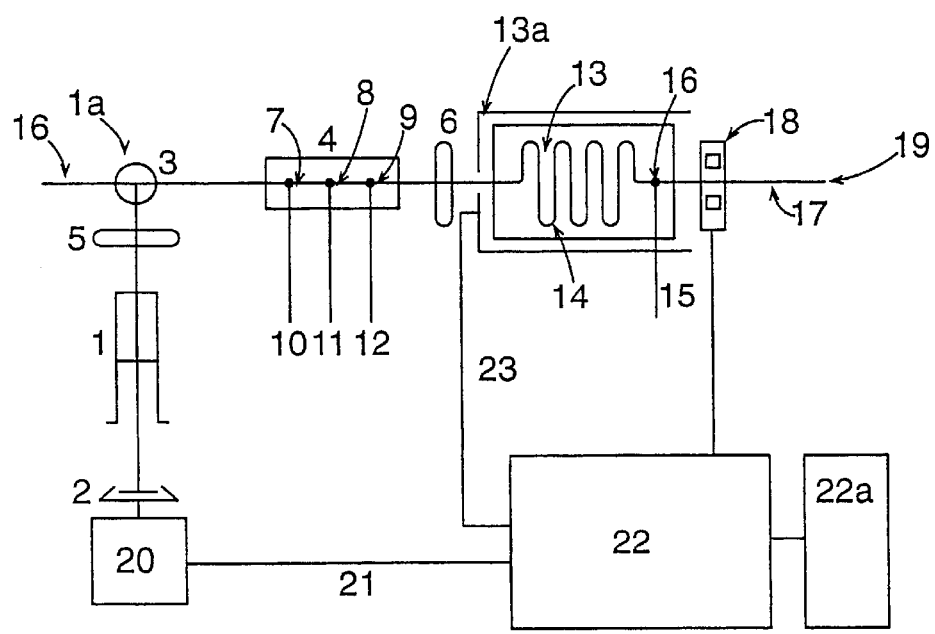
FIG. 1 is a schematic illustration of an embodiment of the present invention, including an analysis cartridge inserted in a module.

The following terms and phrases are used herein:

"Affinity species" means a molecule such as a protein, peptide, or nucleic acid capable of selective or specific binding to another affinity species or to a cell or cell surface. Two affinity species that specifically bind to one another are together referred to as a specific binding pair, and each member of that pair is a member of a specific binding pair. Additional examples of affinity species include selections and ICAMS, receptor ligands, antigens, antibodies, biotin and avidin, etc.

"Capture species" refers to an affinity species that is member of a specific binding pair that is used to bind and thereby "capture" a cell carrying (typically on its surface) the other member of the specific binding pairs, holding it in place for a period of time. When the capture species must function in the presence of shear forces, it should have a sufficiently high affinity for the other member of the specific binding pair to achieve the desired effect for the test. It is generally believed that a multiplicity of bonds (or plurality of binding pairs) is involved in the attachment of a cell to a surface with affinity molecules.

"Capture zone" refers to (i) a discreet, separate and/or defined region of a surface or substrate to which a capture species is directly or indirectly affixed (e.g., by linking species such as biotin-avidin); and/or (ii) to a discreet, separate and/or defined region of a surface or substrate that is composed of material that nonspecifically binds cells, e.g., by hydrophobic interactions, to facilitate cell capture thereon. Textured surfaces can be used as "settling surfaces" to position cells in depressions as they settle. Textured surfaces and nontextured surfaces can also be made of materials that nonspecifically bind cells or contain affinity molecules that bind cells; such textured and nontextured surfaces surfaces can therefore contain capture zones. Textured surfaces, in general, protect cells from removal by shear forces at the air-liquid interface when an occluding air bubble passes through the conduit containing captured cells.

"Cell" or "cells" as used herein refers to all types of cells, including prokaryotic and eukaryotic cells, such as bacterial, fungal, plant, and animal cells. In one embodiment the cells are plant cells, including both monocots and dicots and both angiosperms and gymnosperms, which cells may or may not include the cell wall. In another embodiment the cells are animal cells such as blood cells, including: end stage white blood cell types, such as neutrophils, eosinophils, basophils, T lymphocytes, B lymphocytes, macrophages and their monocyte antecedents; red blood cells and their reticulocyte antecedents; blood platelets and their megakaryocyte antecedents; intermediate forms; progenitor cells; and stem cells that give rise to all of these blood cells; other cells that may appear in the blood or other fluids from time to time such as blood vessel components, e.g. endothelial cells; fetal cells in pregnancy; and bacteria, protozoa and other parasites in blood. While the cells may be live or dead cells, the present invention is particularly advantageously employed with live cells.

"Cell capture" refers to the binding to or deposition on a capture zone by a cell, either temporarily or permanently, so long as the motion of the cell relative to the fluid carrier thereof is delayed. The binding may be specific (e.g., through the interaction of two members of a specific binding pair or nonspecific (e.g., through hydrophobic, electrostatic, or other interactions), and may be direct or indirect (e.g., through means of a linker molecule).

"Computer" as used herein refers to any type of computer, including general or special purpose hardware-based systems that perform the desired functions or steps, as well as combinations of general and/or special purpose hardware and computer instructions. Thus the term "computer" may be used interchangeably with the term "controller" herein.

"Differential flow" or "differentially flowing" as used herein refers to reciprocal flow, flow in which the rate of flow is changed (e.g., increased) and hence the shear forces to which bound cells are exposed are changed (e.g., increased), or any other change in flow properties used to alter the binding, contacting, or depositing of the cells to the imaging field or capture zone. The present invention particularly advantageously implements changes in flow to enrich cell binding (as in reciprocal flow) or to separate weakly bound from strongly bound cells (as in increasing flow after initial binding of cells to separate weakly bound cells from more strongly bound cells).

"Emitted light" in the present invention may be provided from any suitable source, including but not limited to bulbs, diodes, lasers, etc. such as light-emitting diodes, xenon flash tubes, laser diodes, laser tungsten lights, or tungsten-halogen lights. Different light may be created for subsequent interrogating steps by changing the filter for a given light source, changing the light source, or combinations thereof. Thus "different light" refers to emitted lights that differ from one another in one or more properties such as frequency, intensity, direction of travel with respect to the position of cells, etc.

Fluorescent molecules used for cell analysis are a general class of molecules that either directly attach to cells or cell components (DNA, RNA, cytoplasmic proteins, etc.) or can be coupled to affinity molecules with specificity for cell components. Examples of commonly used fluorescent molecules (also called dyes or stains) used for cell analysis include: fluorescein and its derivatives such as fluorescein isothiocyanate (FITC); phycoerythrin (PE) propidium iodide (PI); green fluorescent protein (GFP); rhodamine, Texas red, etc. Fluorescent molecules include macromolecular fluorescent dyes, nucleic acid fluorescent stains; fluorescent probes for divalent ions, and other fluorescent probes for specific target compounds, as discussed below.

Fluorescent molecules as used herein include but are not limited to, α-Phycoerythrin, Green Fluorescent Protein, Phycocyanine, Allophycocyanine, Tricolor, AMCA, AMCA-S, AMCA, BODIPY FL, BODIPY 493/503, BODIPY FL Br2, BODIPY R6G, BODIPY 530/550, BODIPY TMR, BODIPY 558/568, BODIPY 564/570, BODIPY 576/589, BODIPY 581/591, BODIPY TR, Cascade Blue, CI-NERF, Dansyl, Dialkylaminocoumarin, 4',6'-Dichloro-2',7'-dimethoxyfluorescein, 2',7'-dichlorofluorescein, Cy3, Cy5, Cy7, DM-NERF, Eosin, Eosin F3S, Erythrosin, Fluorescein, Hydroxycoumarin, Isosulfan Blue, Lissamine Rhodamine B, Malachite Green, Methoxycoumarin, Napthofluorecein, NBD, Oregon Green 488, Oregon Green 500, Oregon Green 514, Phycoerythrin, PyMPO, Pyrene, Rhodamine 6G, Rhodamine Green, Rhodamine Red, Rhodol Green, 2',4',5',7'-Tetrabromosulfonefluorescein, Tetramethylrhodamine, Texas Red, X-rhodamine; Lucifer Yellow, etc.

Nucleic acid fluorescent stains include, but are not limited to: Acridine Homodimer, Acridine Orange, 7-Aminoactinomycin D, 9-Amino-6-chloro-2-methoxyacridine, BOBO-1, BOBO-3, BO-PRO-1, BO-POR-3, 4',6'-Diamidino-2-phenylindole, Dihydroethidium, 4',6-(Dlimidazolin-2-yl)-2-phenylindole, Ethidium-acridine heterodimer, Ethidium bromide, Ethidium diazide, Ethidium homodimer-1, Ethidium homodimer-2, Ethidium monoazide, Hexidium Iodide, Hoechst 33258, Hoechst 33342, Hydroxystilamidine methanesulfonate, LDS 751, Oli Green, Pico Green, POPO-1, POPO-3, PO-PRO-1, PO-PRO-3, Propidium Iodide, SYBR Green I, SYBR Green II, SYTO 11 live-cell nucleic acid stain, SYTO 12 live-cell nucleic acid stain, SYTO 13 live-cell nucleic acid stain, SYTO 14 live-cell nucleic acid stain, SYTO 15 live-cell nucleic acid stain, SYTO 16 live-cell nucleic acid stain, SYTO 20 live-cell nucleic acid stain, SYTO 21 live-cell nucleic acid stain, SYTO 22 live-cell nucleic acid stain, SYTO 23 live-cell nucleic acid stain, SYTO 24 live-cell nucleic acid stain, SYTO 25 live-cell nucleic acid stain, SYTO 17 red live-cell nucleic acid stain, SYTOX Green nucleic acid stain, TO-PRO-1, TO-PRO-3, TO-PRO-5, TOTO-1, TOTO-3, YO-PRO-1, YO-PRO-3, YOYO-1; YOYO-3, etc.

Fluorescent probes for divalent ions include, but are not limited to:Bis-Fura, BTC, Calcein, Calcium Green-1, Calcium Green-2, Calcium Green-5N, Calcium Orange, Calcium Orange-5N, Calcium Crimson, Fluo-3, Fura-2, Fura-red, Indo-1, Mag-fura-2, Mag-fura-5, Mag-Indo-1, Magnesium Green, Oregon Green BAPTA-1, Oregon Green BAPTA-2, Oregon Green BAPTA-5N, Quin-2, Rhos-2, Texas Red-Calcium Green, Mag-Fura-2, Mag-Fura-5, Mag-Indo-1, Newport Green, Newport Green Diacetate, TSQ, Phen Green; Fluorescein Desferrioxamine, etc.

Fluorescent probe for specific (or "preselected") target compounds or molecules include but are not limited to, those shown in parentheses below following target compounds that can be used in the present invention: :Esterases (Fluorescamine), Peptidases and Proteases (7-Amino-4-methylcoumarin), Phosphatases (Methylumbelliferone Phosphate), Glycosidases (Sugars labeled with Resorufin), Probes for G-Actin (Dnase 1 analogs of macromolecular fluorescent dyes), Probes for Actin (Phallacidin analogs of macromolecular fluorescent dyes), Nonpolar & Amphiphilic membrane probes (Dialkylindocarbocyanine probes), Cell Morphology & Fluid Flow (Hexafluorofluorescein), Cell Viability (FUN-1/Calcofluor White), Ion Channels (BODIPY conjugated dihydropyridines), pH Indicators (SNARF), Signal Transduction (BODIPY FL Thapsigargin), Membrane Potential (Di-4 ANEPPS), Sodium & Potassium Ion (SBFI); Chloride Ion (N-(3-Sulfopropyl)acridiniuim), etc.

"Imaging field" means an area from which light is collected to be analyzed.

"Interrogate" means to actively probe a system such as a cell or an ensemble of cells with energy such as electromagnetic radiation (e.g., light) to obtain information about the system. When a cell passes through the laser beam of a flow cytometer, the cell is interrogated simultaneously for fluorescence, large angle scatter, small angle scatter and possibly for other parameters. In a microscope used to examine cells, for example stained blood cells, the observer simultaneously obtains all optical information. In contrast, in the invention described herein the information is obtained serially or "sequentially." That is, first the field is illuminated (interrogated) with one type of light, then with another, and so on, before moving to the next field of view. With each interrogation, the responses are obtained and recorded or stored for subsequent use. The number of sequential interrogations may be as desired, e.g. at least 2, 3, 4, 5, or more.

"Introducing" of a carrier solution may be carried out by any suitable means, such as by capillary action, injection, or flowing the solution into or through the conduit by means of a pump. Where flowing of the solution is employed, the solution is typically in laminar flow.

"Reciprocating flown" or "reciprocal flow" means to initiate flow in one direction for a period of time and then change (e.g., reverse) the direction of flow for a period of time. The first time period may be the same as or different from the second time period. Preferably, a repeating pattern or periodicity of reciprocating flow is established (e.g., 10, 20, or 40 or more cycles, up to 100 or 1000 or more cycles).

"Reporter species" means a molecule that enables amplification of a signal or generation of a new signal to increase the sensitivity of detection of another species or event. Examples are: enzymes in enzyme immunoassays, fluorophores, chromogenic compounds, chemiluminescent compounds, or generally massive structures such as latex particles, which may contain dye, fluorescent material, magnetic material, etc. The reporter species may additionally include an affinity species to which the detectable group is directly or indirectly joined. Reporter species also include caged probes.

"Response file" means one or more data files, typically stored in a computer memory device, that contains retrievable information on a specific cell. The response file may contain one type of information or a plurality of different types of information. Different information may be contained in a single file or a plurality of separate files that together comprise a response file. A plurality of response files may be organized together or separately as a computer or data file.

"Resultant light" means light reflected by, absorbed by, transmitted through, scattered by, or generated by molecules associated with (or displaced by) cells, such as chemiluminescent or fluorescent molecules.

"Staining" as used herein with respect to cells may be carried out with any stain, such as the fluorescent molecules described above or other non-fluorescent stains or dyes, and is typically carried out by contacting cells to a solution containing a staining agent such as a fluorescent molecule or dye for a time sufficient for the staining agent to bind to a part of the cell or be taken into the cell, for subsequent detection or analysis of the cells. Stain may also be generated as a product of enzyme action within the cell.

"Target cell(s)" refers to a cell or group of cells to be separated from another type of cell or group of cells in a mixture containing both group of cells.

"Washing" as used herein with respect to cells is typically carried out after a staining step, by contacting cells to a wash solution (e.g., an aqueous buffer solution) for a time sufficient to remove excess stain (e.g., nonspecifically bound stain or background stain) so that the stained cells, cell components, or features may be subsequently detected.

2. Methods and Apparatus

In carrying out the methods described herein, program instructions may be provided to the computer to produce a machine, such that the instructions that execute on the computer create means for implementing the functions specified herein. The means for implementing may also be carried out by hardware devices, or combinations of software and hardware.

The methods and apparatus of the invention are primarily described with reference to capture zones below. However, it will be appreciated that these methods and apparatus can be adapted to embodiments employing settling of cells on a substrate in a routine manner.

A schematic illustration of one embodiment of the invention is provided in FIG. 1. In this figure, a sample containing suspended cells (not shown) is introduced at opening 19 in tubing 17. A syringe 1 containing air is driven in either direction by a suitable high precision fluid delivery device or pump, such as a syringe pump drive. Alternatively, the syringe and a portion of the conduit connected to it can be filled with an inert drive fluid or with water to minimize compliance in the fluidic system that could result if the volume of air is relatively large. Syringe pump drive 20, consists of a stepper motor and a micrometer-type lead screw or worm gear assembly (not shown). The syringe pump drive 20 is activated by signal line 21 from computer 22 which is connected to user interface 22a. The user interface is a control module which will typically include a keypad, display or monitor and a speaker. When it is time to draw in a sample, the syringe pump drive 20 pulls the syringe into "withdraw mode", and a precise amount of sample is pulled into tubing 17. This tubing could be disposable and could contain an anticoagulant, such as heparin, in dry form on its walls. Typically, a 1–10 microliter (1–10 cubic millimeter) sample will be drawn.

Depending upon the type of analysis that is to be performed, any of a variety of possible steps could precede the intake of sample, as will be discussed. When tubing 17 is filled with the appropriate amount of sample, the pumping then stops. The volume of sample drawn into tubing 17 is a function of the number of steps delivered by the stepper motor in response to the computer command via signal line 21. At this point, an audible beep may be provided to signal the operator. The operator then removes the sample tube or liquid sample drop from the vicinity of tubing 17 and may, if required, wipe the outside of tubing 17 with a small piece of absorbent material to remove excess sample. The operator then pushes a button to start the test. When this button is pushed, the sample is drawn further into the tubing 17 and travels toward analysis cartridge 13, as shown in FIG. 1. Analysis cartridge 13 (discussed in detail below) is a self-contained disposable element and connects to the fluid delivery lines of the cell analysis instrument. The cartridge consists of tubing 17, an optional "T" connector 16 with extension tube 15 for attachment to another syringe pump that introduces air into the flowing stream at precise intervals if segmented flow is employed, conduit tubing or fabricated conduit 14 and an optional hydrophobic filter 6 if it is necessary to isolate possible biohazardous samples. The connection of analysis cartridge 13 to the instrument is to the left of hydrophobic filter 6 at manifold module 4 and at line 15 which leads to another syringe pump (not shown). Hydrophobic filters will pass air but not liquid. Other components of the system are: "T" connections 7, 8, and 9 in module 4 where additional reagents and/or wash solution can be delivered to analysis module 13 through lines 10, 11, and 12 that lead from additional independent precision pumps; optional two-position valve 1a that switches to connect syringe pump to either line 3 or to air line 1b; optional hydrophobic filter 5 that protects syringe pump 1 from any accidental backflow of liquid; connector 2 that couples the plunger of syringe pump 1 to pump drive 20; and flow sensor 18 which is typically only one of many such sensors situated at various points in the instrument along the flow path.

Figure 2:
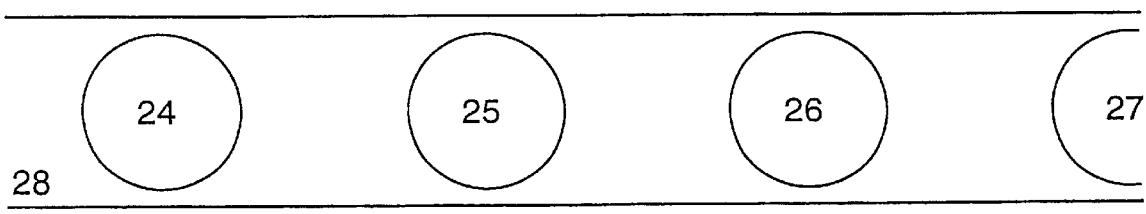
FIG. 2 is a top plan view the capture zones in a conduit of an analysis cartridge employed in an apparatus of FIG. 1.

Analysis cartridge 13 is held by module 13a, which is a portion of the instrument that physically positions analysis cartridge 13, reads optically or magnetically encoded information on analysis cartridge 13, regulates and adjusts temperature of analysis cartridge 13, and monitors events at the capture zones by means of arrays of photosensitive elements. FIG. 2 shows the top view of the bottom of a rectangular conduit 28 of an analysis cartridge. Capture zones 24–27 are shown.

Typically, a flow sensor consists of one or more light emitting diodes (LED's) and photodetectors or photodiodes. Light from the LED's passes through the walls and center of tubing 17 (or other portions of the flow path) and is detected. The signal will change when the air-liquid interface of the sample flows past and will also be influenced by the presence of suspended cells which scatter light. A variety of optoelectronic detection schemes are possible to monitor the flow, for example as taught by Oberhardt and Kopelman in U.S. Pat. No. 4,100,797. The important consideration is not only to verify the flow rate, which is set by the computer, but to check along the length of the liquid sample segment for breaks or for large air bubbles. The liquid sample segment is then sent into analysis cartridge 13.

Figure 3:
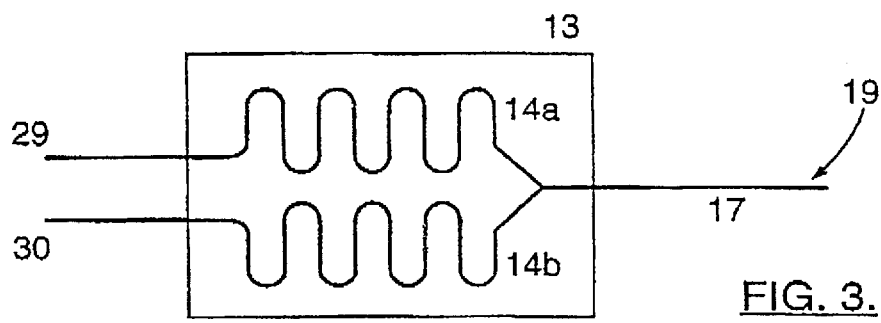
FIG. 3 illustrates an alternate embodiment of an analysis cartridge of the present invention.

Analysis cartridge 13 is typically a disposable single-use item and could be any of a variety of types. This analysis cartridge could also contain two main conduits 29, 30, as is shown in FIG. 3, where the liquid stream of sample flowing through tubing 17 is split into two streams, each of which is driven by a separate syringe pump and sent to a separate conduit 14a, 14b for analysis. This allows the same sample to be tested simultaneously under different conditions, as will be described. Upon entering the analysis cartridge, the sample may be subdivided into smaller segments by injection of air at "T-junction" 16 prior to analysis. As an alternative, a 2-way valve could be used instead of "T junction" 16. The addition of air to form shorter segments provides segmented or "slug" flow conditions over the major portion of each liquid segment, thus enhancing mixing and randomization of the cells contained in the liquid segments, as opposed to pure laminar flow. Improved radial transport during slug flow conditions was analyzed and described by Horvath, Solomon, and Engasser (I & EC Fundamentals 12: 431, 1973).

Figure 4:
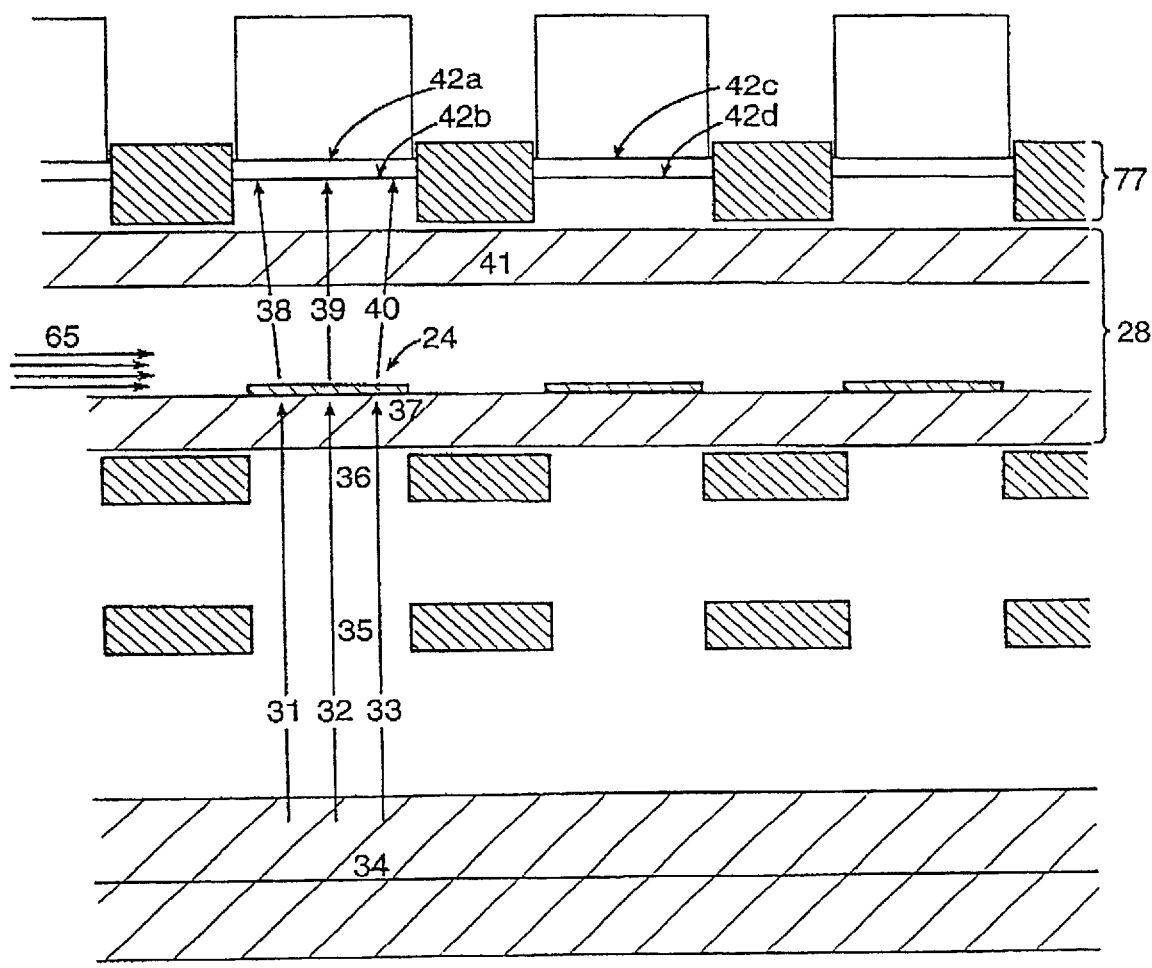
FIG. 4 is a side sectional view of an analysis cartridge of the invention, in place in a module in accordance with FIG. 1.
Figure 12:
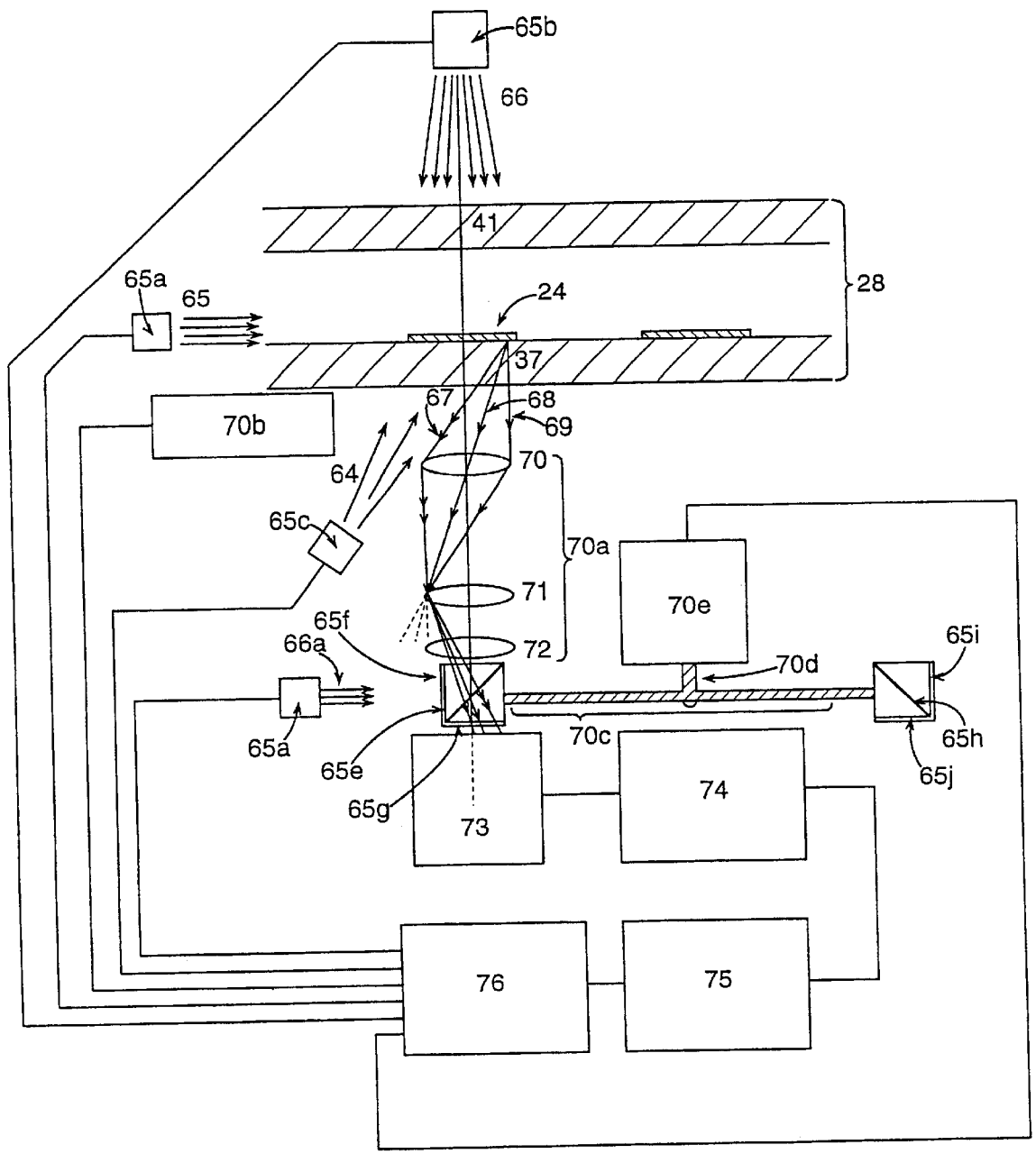
FIG. 12 is a schematic illustration of an apparatus of the invention employing a conduit with a plurality of capture zones and microscope scanning system.

In one embodiment of the invention, as seen in FIG. 1, the liquid segment (or segments) containing cells continues to flow through the cell analysis cartridge 13, which is designated here as a cell capture cartridge. In this cartridge, there are surfaces to which are bound specific receptors, ligands or antibodies, as will be described. These coupled molecules will be designated as capture species. Light passes through the transparent walls of the cell capture cartridge and through the sample, which is further detailed in FIG. 4 (not to scale), light waves (or photons) from one or more light sources shown here as rays 31, 32, and 33 from a single line source 34, which could be a line filament of an incandescent source, an LED, a xenon flash tube, etc., are transmitted through collimating slits 35 and 36 and pass through the transparent bottom 37 of conduit 28 striking capture zone 24. The use of the collimators limits the light to the specific capture zone being interrogated or illuminated, and reduces or prevents the exposure of other fluorophores to light and, consequently preserves the intensity of the fluorescent signal to be elicited therefrom. This same means or other means such as a shutter mechanism for minimizing the exposure of fluorophores to light can be incorporated in all apparatus disclosed herein. Alternatively, excitation rays 65 can be used to excite fluorophores in or on captured cells. Light rays 38, 39, and 40 emitted from the captured cells fluorescent, chemiluminescent, or fluorogenic reporter species (or attenuated light rays from passage through stained cells) then pass through the transparent top 41 of conduit 28, pass through filter 42b, and strike and strike photosensitive array 42a, effecting photon-electron transduction and concomitant electronic signals. 42c and 42d correspond to another set of elements similar to 42B and 42a, set for measurement in a different frequency range. Partition material 77 isolates the detection cells from each other, in addition each detection cell has its own photosensitive array and filter. The photosensitive arrays can consist of photodiodes or charge coupled devices (CCD's) or other photoactive elements. Such elements will be designated herein as photodetectors. The photodetectors are linked to the computer in essentially the same way as shown in FIG. 12, except without the microscope components. There are light sensitive elements, preferably CCD's to store charge, dependent upon incident light intensity and electronics (shift register logic, etc.) to convert the charge to an analog signal (voltage) and subsequent analog-to-digital conversion (as with capture board electronics). The digital signals are then fed to the computer in accordance with standard techniques.

Referring now to FIG. 1, many regions in the flow path of the cartridge 13, designated as capture zones, contain the bound specific receptors, ligands, or antibodies, and can capture cells from the liquid segments as they flow onto these regions. In the conduit of the cartridge 13, cells can be driven to the capture zone surface by the slug flow (segmented continuous flow) fluid dynamics or film transport and less efficiently by the lamina in longer segments undergoing predominantly laminar flow, as will be discussed. After flowing past all of the capture zones, the flow direction of the liquid segment or segments can be reversed by the syringe pump to repeat the path of travel, this time from the opposite direction. This reciprocal flow pattern can be repeated many times, if necessary and can be controlled by the computer 22 via signal line 21. Precise volume delivery by the syringe pump 1 and drive 20 and good dimensional control of the conduit 14 in cartridge 13 as well as proper treatment of the cartridge surfaces, as will be discussed, can provide a high degree of control over flow velocity, shear forces, and fluid dynamics, in general.

In addition, the temperature of the cartridge is controlled by heating elements in module 13a, which heating elements are in turn controlled by computer 22, via control line 23 (see heating/cooling discussion in conjunction with FIGS. 9A and 9B below) to establish reproducible conditions in fluid flow (since the viscosities of liquids are temperature dependent) and to control cell membrane fluidity and the thermal kinetics of antigen-antibody bonding. It is well known that the cell membranes of some cells display "glass transition temperatures" above which the membranes are more fluid and the membrane proteins more mobile and can self-associate or form clusters. As discussed previously, temperature can have a profound effect on antigen-antibody bonds on cell surfaces. During the transit of the liquid segments across the capture zone surface, cells are captured and adhere to the surface. The capture process involves multiple bonds of ligand and receptor between the capture zone surface and the cell surface. During this process, the kinetics of cell capture may be recorded, as will be described. That is, the rate of cell capture in each capture zone and the cumulative number of cells captured can be determined on a real time basis.

Figure 5:
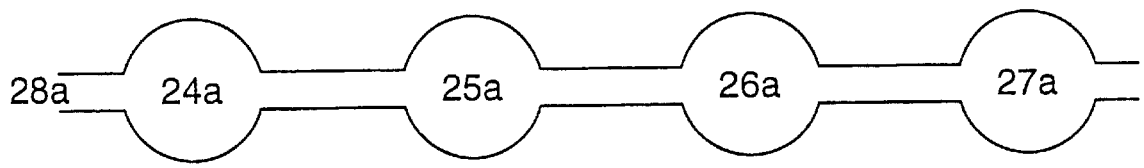
FIG. 5 is an alternate embodiment of the capture zones illustrated in FIG. 2.

Typically, each capture zone is approximately 400 microns in diameter, but this dimension can vary considerably. A 400 micron diameter capture zone has an area of approximately $1.26 \times 10^5$ square microns. This area is sufficient to capture more than 600 cells of 15 micron diameter, the approximate diameter of many leukocytes, providing a reasonably good number of kinetic data points, even if only 10% of the available area becomes filled with captured cells. For a normal sample consisting of one microliter of anticoagulated (e.g. heparinized) blood, a total combined capture zone area of only 1.4 square mm is sufficient to capture all of the leukocytes. A total area of only 0.3 square mm is sufficient to capture all of the blood platelets. However, a considerably larger area of approximately 250 square mm is necessary to capture all of the red blood cells. For a conduit length of 50 mm in length, it is possible to have 10 or 20 to 50 or 70 or more such capture zones of 400 micron diameter, assuming that adjacent zones are spaced at approximately 300 microns apart. Thus it is possible in a 50 mm-long conduit to perform as many as 10 or 20 to 50 or 70 more independent cell analysis tests based on surface-mediated cell capture alone. This does not take into account the ability to measure other parameters at capture zones, such as additional surface antigens. Insofar as applicant is aware, there is currently no other technology that can perform so many cell analysis tests on a given sample. It may be desirable to space capture zones further apart to provide better isolation of photodetector arrays from stray light originating at adjacent capture zones. Moreover, the conduit need not be straight and can have a series of turns, as illustrated by conduit 14 in FIG. 1. Conduits of various internal dimensions and shapes can be employed, as seen in an alternative embodiment in FIG. 5, where conduit 28*a* narrows considerably between capture zones 24*a*, 25*a*, 26*a*, and 27*a*, etc. For blood cell analysis using this technology with a conduit of rectangular cross section, the conduit height could be as little as 40 microns to enable the cells to easily pass over or around a monolayer of captured cells but for practical reasons may be much greater. Heights of rectangular conduits of greater than 100 microns and even in the 250 micron range would be suitable. If blood platelets are being studied, especially at high shear rates, it may be necessary to use conduits of greater internal height to prevent platelet plug formation from easily clogging the system, unless this effect is desired. Many embodiments of the invention are possible, with regard to fluid channels. The channels could be wide at the capture zones and thinner elsewhere or have the least cross sectional area at the capture zones or could be uniform throughout. It is also possible to fabricate a cylindrical conduit with one continuous capture zone on the surface of the internal wall, as will be discussed.

Figure 6A:
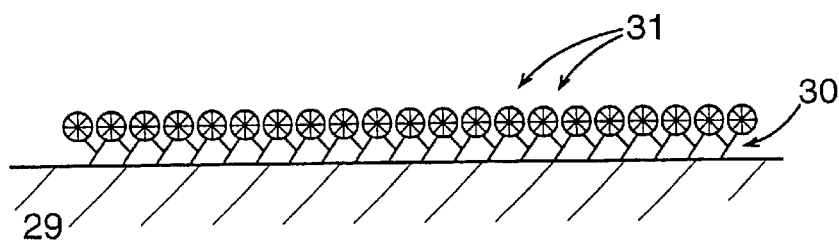
FIGS. 6A–6C illustrate a capture zone of the invention employing competitive binding with a reporter species.
Figure 6B:
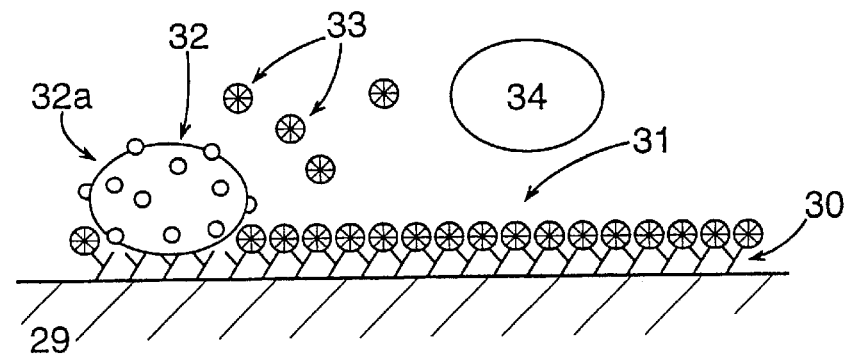
Figure 6C:
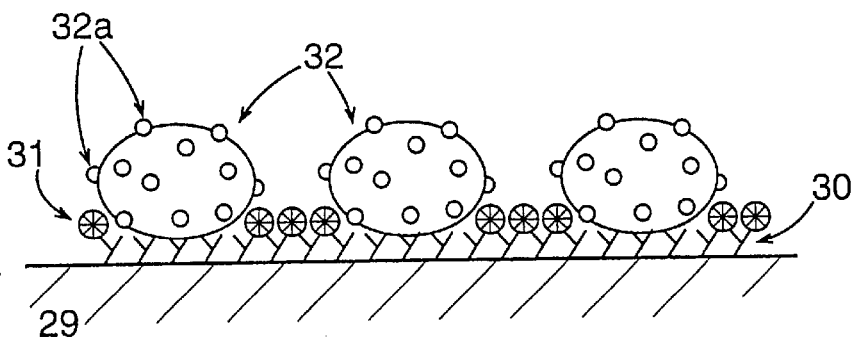

Since each capture zone is preferably monitored, the attachment of a cell can be recorded. One embodiment is shown in FIGS. 6A, B, and C. In FIG. 6A, specific receptor molecules 30 (e.g. antibody molecules with high affinity for the surface groups of interest on the cell) are covalently coupled or otherwise strongly attached to the surface 29 of the conduit at the capture zone. To the binding sites of these receptor molecules are bound molecules 31. These molecules 31 are essentially identical to cell surface group 32*a* found on cell 32 in FIG. 6B, except that these ligand molecules are themselves covalently coupled or otherwise strongly attached to either fluorescent molecules or to particles (e.g. latex beads) that contain fluorescent molecules to form a reporter species. This composite species consisting of ligand and label is designated as 31 in FIGS. 6A, B, and C. To facilitate favorable cell capture rates, the affinity of the receptor (e.g. antibody) for the cell surface ligand should be greater than that for the initially bound ligand. As seen in FIGS. 6A and 6B, the cells displace the initially bound molecules as their cell membrane ligands attach to the capture zone receptors. In FIG. 6B, cell 34 does not possess cell surface group 32*a* and therefore does not displace the initially bound molecules. As viewed by the photodetector or photodetector array, when a cell is captured, fluorescent material is lost from the surface, and a dark spot appears on the capture zone surface. In FIG. 6B, the fluorescent material 33 that is lost is diluted by the volume of the flowing liquid, and its signal soon becomes greatly attenuated. Each time a cell is captured, the dark area grows (see FIG. 6C). The fluorescent signal intensity versus time is easily determined for each capture zone, and thus the kinetics of cell capture can be readily measured. Other optical configurations are possible, for example the excitation illumination could be coupled into and sent longitudinally along the bottom 29 of the conduit and the evanescent wave read from above, thus minimizing the optical signal (noise) from released fluorescent material 33.

3. Cell Rolling

The methods and apparatus described herein can also be used to study "cell rolling", a traveling adherence phenomenon on blood vessel walls observed under appropriate laminar flow conditions with certain types of blood cells (e.g., white blood cells, platelets) that roll from receptor to receptor on the vessel wall endothelial cells. In such a case, a rolling cell would produce a dark streak upon removal of fluorescent material, thus leaving a track. It should be noted that this approach is a macroscopic approach to obtaining information about cell rolling, with an ensemble of rolling cells without actually using a microscope to image individual cells. Receptor molecules of more than one type can be used in the same capture zone. For example, selections and ICAMs (intercellular adhesion molecules) can both be coupled to the capture zone surface. A system can also be fabricated where white blood cells roll along the surface of the capture zone by binding and unbinding to the selectin molecules with their selectin receptors could also become stimulated, thus activating cell surface integrin which would readily bind to ICAMs attached to the capture zone surface, thus capturing the cell and bringing the rolling to an abrupt halt. Capture zones of large area may be used to quantify this phenomenon. To read the fluorescent signal, the light source need not be active all of the time. To preserve fluorophores and to conserve energy, the light source could be pulsed periodically. Possible light sources include xenon flash tubes, laser diodes, and LEDs. Appropriate optical filtering should be employed post excitation to exclude light at the excitation band frequencies but admit light at the fluorescent emission frequency. With each light pulse, the fluorescent signal is read, and compared with previous signals. Specific computer programs can be applied to perform signal averaging and comparisons. Time resolved fluorescence measurement can also be used with the appropriate fluorophores.

An entirely different way to visualize rolling cells or cells that are captured is to image one or more entire capture zones with a CCD camera or with a multiplicity of CCD cameras or CCD elements. If this is done, pixel analysis with appropriate programs will provide the requisite information on cell attachment by subtracting rapidly moving cells from the image each time that flow is established or reestablished and leaving or adding the signals from captured or detained cells. By kinetic analysis at capture zones, it may become possible to estimate the population sizes of specific types of cells. This may be achieved by comparison of the frequency of capture of a particular cell type with that of a standard control cell at a known concentration.

Systems and processes for flow control are also utilized. Many such systems and processes are possible. For example, the flow rates may be preset at a desired level to maintain a designated narrow range of flow velocities and wall shear rates. Alternatively, flow rates can be programmed to increase or decrease progressively. Of particular advantage is the use of feedback controlled flow rates. Signals from cell capture at one or more cell capture zones may be used as input signals to the computer to adjust flow rates to maximize capture at a particular capture zone or at a number of zones.

4. Capture Zones and Post-capture Staining

Figure 7A:
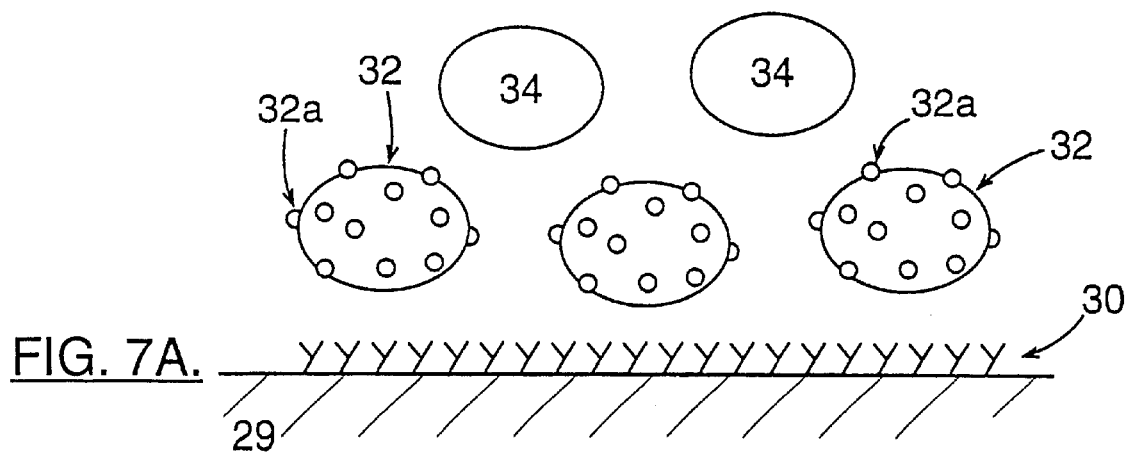
FIGS. 7A–7C illustrates a capture zone of the invention employing sandwich binding with an affinity species or affinity reporter.
Figure 7B:
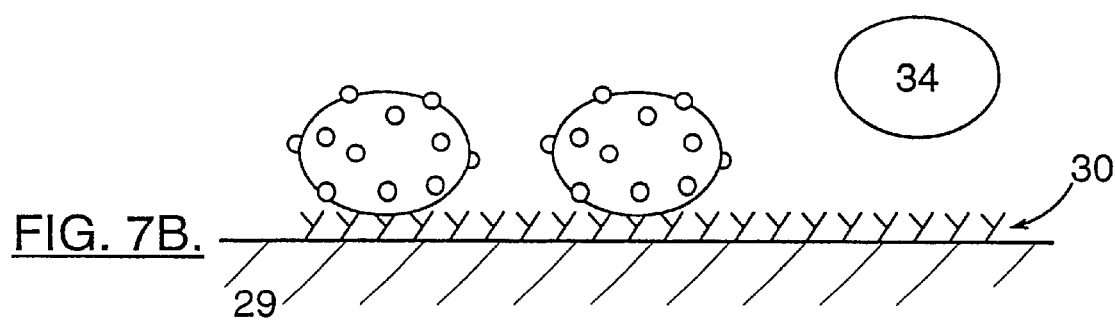
Figure 7C:
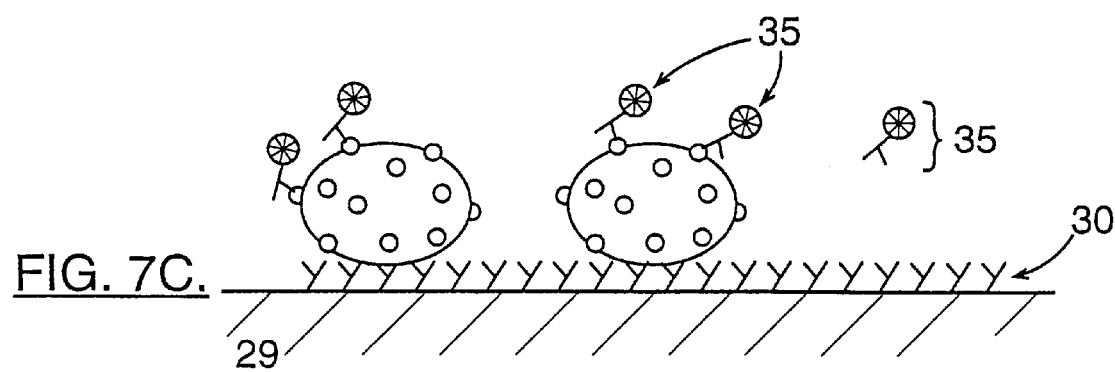

As shown in FIG. 7, another way to determine the kinetics of cell capture is to flow the cells onto capture zones that have a directly or indirectly surface-coupled capture species 30 to capture the cells. In 7A, cell types 32 and 34 are introduced. In this embodiment, the liquid sample segment (or segments) containing the cells is allowed to dwell or to flow slowly or to undergo reciprocating flow or to lay down film (as will be explained) at the capture zone surface. As shown in 7B, cell 32 is captured, but cell 34 remains in suspension. The liquid segment (or segments) is then removed and followed by a liquid reagent segment containing species 35 in FIG. 7C. Species 35 consists of the same species as species 30 that used to capture cells at the capture zone surface, except that this species is coupled to a fluorescent molecule or to a particle (e.g. a fluorescent particle). Thus, the labeled species 35 is unbound and contained in the bulk solution of the reagent segment introduced in FIG. 7C. The use of free fluorescent labeled capture species in the reagent segment enables the upper, unbound, surface of captured cells to become labeled progressively with fluorescent material, thus producing bright areas where cells are captured.

The use of reagent segments to flow over captured cells allows post-capture processing of the cells. Another variation of this process is to use biological stains such as Wright-Giemsa stain, methyl green, and others in reagent segments to stain captured cells. In this case, the cells that become stained will strongly absorb light at the frequency appropriate to the particular chromophore used. The reagent segments can be introduced periodically to process captured cells, can be deployed at selected flow rates or held at zero flow rate at capture zones, if desired. The reagent segments can be followed by wash segments containing buffer to remove residual, free reagent from the cell capture zone. Captured cells can be stained and washed once, or can be stained and washed and the process repeated one or more times with different stains. A wash step or permeabilization step can preceed the staining step if desired. All of the staining steps may be prior to the detection or analysis steps, or one or more staining steps can be carried out between first and subsequent detection and analysis steps. Thus the present invention provides great flexibility in the capture, staining and detection or analysis of cells.

5. Measurement of Antigen Concentration and Other Methods of Measuring Cell Capture A variety of approaches or schemes can be used in accordance with the invention to measure total antigen concentration. From these data and cell capture rates it is also possible to measure cell concentration. One such scheme is to introduce a known amount of free antibody into the sample early on so that this antibody can bind to the cell with the antigen of interest. This antibody is identical to the antibody coupled to the capture zone surface and therefore competes with the latter by rendering cell surface antigenic sites unavailable for binding to the capture zone antibody. Thus, the comparison of cell capture kinetics with and without free antibody added to the sample provides a measure of the antigen loading per cell and cell concentration. That is, if in the absence of added free antibody, a particular rate of capture of the cell is observed, the ratio of this rate to the rate observed in the presence of free antibody is a function of cell antigen loading and of cell concentration. For a given amount of antibody added to the sample, if the cell concentration were increased, the inhibition of cell capture would be proportionally decreased. Scatchard plots have been applied to analogous data in equilibrium dialysis data to determine cell antigen loading. In a system with multiple capture zones, it is possible to apply this powerful technique to many cell types and to many antigenic sites simultaneously by adding as many different types of free antibody molecules as desired.

It is also possible to use a variety of other schemes to measure cell capture. For example, free antigen (or idiotypic antibody) can be coupled to any of a variety of reporter species, such as a fluorescent molecule or particle, an enzyme, a chemiluminescent species, etc. This free labeled antigen should be chosen to be identical to the species coupled to the capture zone; which is, in this case, unlabeled antigen. The free labeled antigen then competes with the cells for binding sites on the capture zone surface. The cell capture rates are, in this case, determined by the amount of labeled antibody that binds to the capture zone surface. Comparison of the capture rates at different concentrations of labeled antigen provides ratios that can be used to determine cell concentration.

Another such measurement scheme employs a known amount of a first free labeled antibody added to the sample containing the cells of interest with the cells being captured at a first capture zone containing a second antibody directed at a different epitope. The excess first (labeled) antibody, the amount of which is determined by the antigen loading and cell concentration, is then captured at a second capture zone and quantified. From the resultant first antibody kinetics at different antibody concentrations and the observed cell capture rates as compared to controls, cell antigen loading and cell concentration may be determined.

6. Cell Separation

Another use of the invention is to separate a small number of cells of one type, or "target cells", from a large population of cells of another type. This can be achieved through the use of a multiplicity of capture zones that are physically isolated from one another and contain the same capture species. For example, if these capture zones are situated in parallel conduits, they can be isolated from one another with valves. First, the sample is allowed to flow repeatedly across one capture zone. After the capture zone is substantially filled with cells from the sample, the liquid segment containing the cell sample is pumped out, and a buffer is pumped in, either with a shear field that increases with time or at a known wall shear rate sufficient to dislodge the cells from their respective capture species molecules. The volume of buffer required is relatively small, and a reciprocating flow pattern can be used to transport the buffer across the capture zone alternately from either direction. When the cells have substantially resuspended, as indicated by the capture zone optical detection system, aided by appropriate programs from the computer, the resuspended cells are then introduced to a second capture zone. This process can be repeated many times to obtain a multistage enrichment of cells at the final capture zone. It is also possible to introduce the cells in the sample to one or more capture zones containing a second capture species with different specificity than the first to target cells based on two cell membrane markers. Additional capture species with yet other specificities could similarly be used on the surfaces of these or other capture zones. In this type of system, optical monitoring can be achieved at a few capture zones or over a small portion of a single large capture zone to provide an optical detection system for measurement of cell capture kinetics without disturbing the system via release of massive amounts of labeled species.

Another system is a series arrangement of capture zones in a single conduit with adequate spacing between them. The liquid segment containing the cells is pumped back and across the first capture zone until a sufficient number of cells are captured. The liquid segment is then pumped out and replaced by buffer. This buffer is pumped back and forth at an appropriate velocity to remove the cells by application of sufficient shear forces. This buffer segment then advances to the second capture zone where the flow slows substantially to allow cell capture. When this process has gone essentially to completion, the buffer is pumped out along with any extraneous suspended cells and replaced by new buffer and the process repeated. Eventually, a final preparation of captured cells is obtained. This preparation can be removed with fresh buffer under appropriate shear conditions and saved. It may be necessary, depending upon the type of cell to be recovered, to perform this process at low temperatures, e.g., at 4° C. to minimize cell disruption or possible unwanted cell activation. Alternatively, a lytic agent can be pumped in at a sufficiently low flow rate to recover only the cell contents, leaving other cell components such as the cell membrane behind. The suspended cell contents can be pumped out of the system and subsequently examined microscopically or analyzed using DNA amplification and identification techniques, etc.

Prior to separating the cells, the capture zones may be prepared by the user so that a particular capture species, for example a unique monoclonal antibody, can be affixed to the capture zone surface. This is achieved by the user in a variety of ways, for example using a simple incubation procedure to bind the antibody to protein A molecules that had been previously coupled to the capture zone surface or using a biotinylated antibody to bind the antibody to avidin molecules that had been previously coupled. Covalent coupling of capture species to the capture zone surface may be achieved with any of a variety of chemical coupling techniques that are well known in the art of coupling proteins and other molecules to solid supports. This subject is treated in detail in various textbooks (e.g. Bioconjugation. M. Aslam and A. Dent. Stockton Press, New York 1997), in professional journals (e.g. Clinical Chemistry, The International of Laboratory Medicine and Molecular Diagnostics, published by the American Association for Clinical Chemistry, Wash. D.C.) and in immunological supply catalogs such as the Pierce Company catalog (Pierce Company, Rockford, Ill.). Capture zones can be generated by deposition of appropriate bifunctional molecules that can couple to the surface material by covalent bonding at one end and to the desired species at the other. These molecules can be deposited precisely with nanoliter pumping systems and/or ink jet apparatus. Capture zones prepared with a multiplicity of different capture species can be easily and rapidly generated in this manner. Alternatively, the capture zones could be supplied to the end users already prepared chemically with derivitized surface groups. Spacer molecules of prese- lected length could also be coupled to the surface groups beforehand. If biotinylated antibody is bound to surface-coupled avidin receptors or antibody bound to surface coupled protein A, care should be taken that the shear forces are kept below the level that would rupture the avidin-biotin or protein A-antibody bonds.

As noted previously two different cell populations can be separated in a single capture zone by allowing the cells to bind to the capture zone (specifically or nonspecifically), and then increasing the rate of flow rate of the carrier solution. Increasing the rate of flow of the carrier solution (from either essentially no flow to a greater rate of flow, or from a given rate of flow rate to a higher rate of flow) increases the shear forces to which bound cells are exposed. Weakly bound cells will be removed by the increased shear forces while more strongly bound cells are not. With a pump, particularly a syringe pump, the flow rate can be controlled sufficiently to enable a variety of different separation procedures with routine adjustment.

7. Cartridge Apparatus

Figure 8:
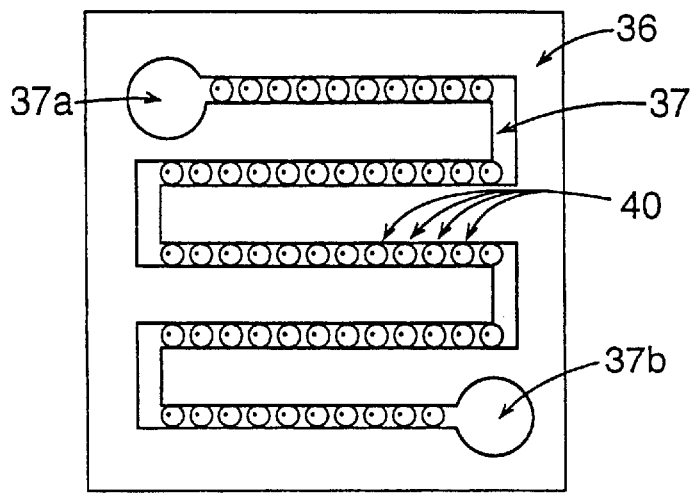
FIG. 8 is a component of an analysis cartridge of the invention.
Figure 9A:
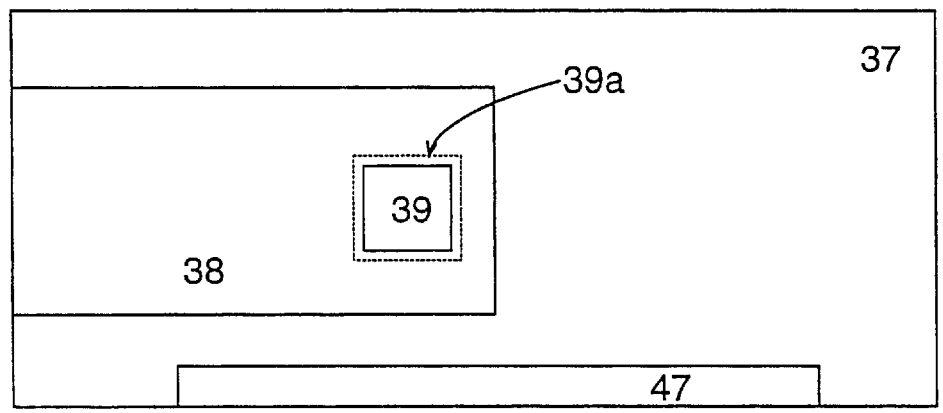
FIG. 9 illustrates an analysis cartridge of the invention incorporating the component of FIG. 8.
Figure 9B:
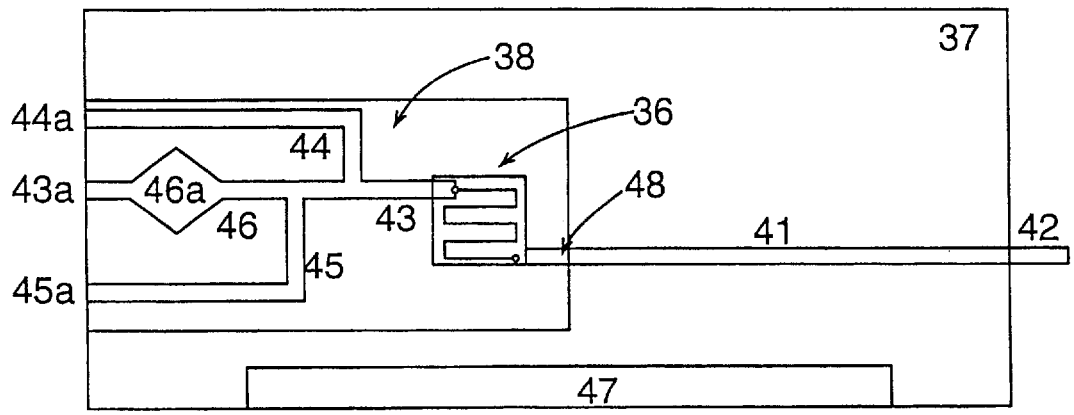

FIGS. 8 and 9 show a disposable element for cell capture analysis that can be used to characterize cells conveniently. In FIG. 8, a micromachined or injection molded transparent flat unit 36 is shown with an open channel 37 of uniform depth and terminal ports 37a and 37b in the form of circular areas, also of the same depth as channel 37. The unit 36 may be formed of glass, fused quartz, polystyrene, polyester, cellulose acetate or other suitable material. One or more capture zones 40, equipped with bound reagents or derivitized groups are easily formed in the open channel as has been described. It should be recognized that some materials will nonspecifically capture molecules and/or cells. In the field of immunoassay, surfaces are often treated with "blocking agents" to prevent nonspecific attachment. These agents include bovine serum albumiin, human serum albumin, milk proteins, serum proteins and other proteins and agents. Blocking agents may be used in conjunction with the present invention to minimize or eliminate nonspecific binding. Referring now to FIG. 9A, a base 37 of stiff material, such as polystyrene, polyester, or other suitable optically transparent polymeric material, cut from a larger sheet or roll stock of the same material is shown with hole 39 formed by cutting or punching. Dotted lines 39a show the position and size of unit 36 in the assembled disposable element, as shown in FIG. 9B. The disposable element, depicted in FIG. 9B, consists of unit 36 sandwiched between unit 38 as the top layer and the base 37 as the bottom layer. The assembly can be held together by pressure, e.g. by a rigid frame (not shown) that forces the three layers together with a compressive force in considerable excess of the pumping pressures or by using adhesive bonding, solvent bonding, or ultrasonic welding of the three components, depending upon the materials chosen. Rectangular unit 38 is a micromachined or injection molded cover for unit 36 and also serves as a manifold, since it also has open channels, as shown in FIG. 9B. Placing and affixing unit 38 onto unit 36 provides closed conduits for flow and cell analysis. Similarly, placing and affixing unit 38 onto base 37 provides closed conduits for connection to pressure sources, e.g. syringe pumps for reagent delivery and fluid movement for cell analysis. Unit 36 also provides fluid connectivity with the terminal ports 37a and 37b of channel 37, while converting the latter into a closed conduit. In FIG. 9B, to the left of unit 36, is conduit 43 that connects with terminal port 37a of FIG. 8 at one end and forms conduits 44, 45, and continues as 46 at the other end. Conduit 46 may contain a region 46a of larger cross sectional to house an absorbent pad that can be used for final disposition of the sample and therefore function as a receptacle for biohazardous material. Terminal openings 43a, 44a, and 45a provide connectors to mate with a plug (not shown) that contains three appropriately positioned rigid, e.g. stainless steel, tubes. At the right of unit 36 in FIG. 9B, a cylindrical sample tube 41 is inserted into the opening 48 in unit 38 and typically extends beyond the end of base 37. The opening 42 of sample tube 41 is shown at the right, and it is through this opening that the sample is introduced. Area 47 in FIGS. 9A and 9B is for placement of an optically or magnetically readable code portion such as laser-etched indicia or a magnetic strip that identifies the disposable element and provides instructions to the analyzer to simplify the number of independent user operations. The cell analysis cartridge is inserted into and thereby secured to a module (FIG. 1; 13a) that positions the cell analysis cartridge in the field of view of the microscope objective. The module preferably contains computer-controlled translation in the X and Y directions, and preferably also in the Z direction to achieve automatic focus. The module is kept at a set temperature, acting as a temperature block or reservoir, and may optionally position air vents for heating and/or cooling the analysis cartridge. Additional connections to the module may be made with flexible tubing and the like in accordance with known techniques to permit movement of the cartridge while also allowing the desired flow conditions to be achieved therein.

A continuous capture zone provides an advantageous system for cell separation as shown in FIG. 10. This system may be contrasted with the system described by Snyder, Oberhardt, and Olich (U.S. Pat. No. 4,028,056; Substance Separation Technique). In this prior system, a particulate portion of a mixture including a liquid portion is separated by means of a continuous process, where a segmented stream of liquid containing particulates is sent through an open bore conduit having an internal surface of porous configuration for permeation thereof by dissolved species but not by the particulates. The net effect is that after traveling a sufficient distance through the conduit, the dissolved species, having spent part of its total residence time in the pores, lags behind the particulates. Since dissolved species and particulates are now separated spatially and occupy separate liquid segments, it is a simple procedure to activate a valve to divert the dissolved species or to divert the particulates, thereby achieving separation. The system shown in FIG. 10 is an embodiment of the present invention and has the surprising result that the particulates, or more specifically a particular cell type, lags the dissolved species and lags behind the other cells, such that cells of this particular type will eventually become separated from the others and can be selectively removed by switching a valve to divert the stream. This system employs a hollow bore conduit, preferably with a textured surface, and with ligand and/or receptor molecules coupled to the conduit wall. These coupled molecules have specific binding capacity for receptor and/or ligand, respectively, on the cell surface. Thus the cell type for which the specificity exists will be retarded in its transit through the conduit, even if it is not captured. In fact, flow conditions may be optimized with this system to minimize capture and maximize gradual retardation of the forward movement of these cells. It is desirable to use textured surfaces (or a highly wetable surface material) to minimize the scrubbing effect of occluding air bubbles that separate the liquid segments, since this scrubbing effect can aggressively dislodge captured cells.

In FIG. 10, conduit 49 with inlet 50 and outlet 55, "T"-junctions 51 and 52, and a continuous (or discontinuous) capture zone cell delay system as a coating on the internal wall of conduit 49. FIG. 10C shows a capture zone 49a, consisting of surface-coupled antibody molecules with specificity for the surface markers on the cells of interest. Antibody is coupled to surface 49b. FIG. 10D shows a more detailed embodiment, where the capture zone includes a positioning molecule 49c chemically coupled (in this case) to surface 49b and subsequently linked via a second molecule 49d to specific antibody 49e. It is also possible to use avidin for 49c and biotin for 49d, along with coupling agents well known in the art. A continuous stream of buffer is pumped into inlet 50, followed by air segmentation at T-junction 51 and the addition of buffer at T-junction 52. The addition of buffer is interrupted when two segments of a sample containing cells are sent into T-junction 52 at the same flow rate, followed immediately by buffer solution. The sampling can be achieved by a suitable piece of tubing connected to the upstream side of a peristaltic pump, where the open end of the tubing is situated in a reservoir of buffer and then allowed to contact the sample for a designated period of time before being replaced in the buffer reservoir. Alternatively, if a syringe pump is employed, a valve can switch to a sample line to draw in the sample and then switch back to the buffer line. In either case, it is important to insure that the stream of sample that is pumped is separated from the buffer by air segments. Since air segments are used, it is desirable to adjust flow rates and/or use textured surfaces to minimize the scrubbing of cells by occluding air bubbles. Sample segments 53 and 54 move through conduit 49, as shown in FIG. 10A. The continuation of conduit 49 is shown in FIG. 10B, where the sample in segments 53 and 54 has separated into two sets of segments. The first set, 53a and 54a contains the cells with the surface groups recognized by the affinity molecules coupled to the solid support. The second set, 53b and 54b contains the remainder of the cells. Light source 56 and photodetector 57 determine the presence of cells in the segments for subsequent removal of the desired segments via a stream-switching valve (not shown). The light source 56 would typically be a near-infrared emitting LED with a collimator to define a narrow beam prior to entering the conduit wall. The detector would typically be a photodetector or photodiode with a filter to pass only near-infrared energy. The LED can be operated at steady state or can be pulsed at a frequency of sufficient magnitude so as not to interfere with the photodetector amplifier signal sampling rate by the computer. The use of emitter-detector pairs as described enables the detection and analysis of air and liquid segments and of particulate material, i.e. cells, suspended in the liquid.

FIG. 11 shows a continuous flow cell separation of the type shown in FIG. 10 connected to a cell counting system. In FIG. 11, the initial buffer stream enters the inlet 50 of conduit 49. Air enters through T-junction 51, and an aliquot of sample separated before and after by air segments and then buffer enters at T-junction 52. In this embodiment, coil 62 contains the continuous capture zone cell delay system. Emitter 56 and detector 57 provide a signal to computer 61 that triggers valve 58 to send the cells that are desired to be subjected to further analysis into branch 60, which leads to flow cytometer 63 (or other analysis machine, such as a DNA analyzer). Other cells and buffer are sent through branch 59. This system allows further analysis, e.g. counting and sizing of the cells that have been separated based on surface group-dependent affinity. The cell counting system shown here could be a conventional system of the types of high speed direct cell counting systems well known in the art of flow cytometry that employ electrical impedance measurement or light scatter measurement or optical density or transmittance measurements.

Alternatively, the direct cell counting system could employ a special flow cell for low flow rate, low shear conditions (not shown). In such a flow cell, the stream of cells, properly diluted to avoid coincidence counting, is divided evenly at the entry port into a multiplicity of tiny flow cells. As many as 30 or 40 or even 100 or more flow cells are possible, thus allowing cell counting in parallel to minimize the time required for the slow cell throughput at low flow rates. The low flow rates have two advantages: the tendency of some cells, such as blood platelets, to become activated by high shear forces and stick to the walls is minimized, and the slower transit times allow a longer look at each cell for classification purposes. In such systems, it may not be necessary to lyse specific cells, such as the red cells, to improve the signal from the desired white cells. Multichannel flow cells can be fabricated as a disposable element and used for low flow rate counting of cells.

Some attention should be given to the mechanisms associated with capturing cells at capture zones. As has already been mentioned, various mechanisms can result in movement of cells away from a designated location, i.e. a capture zone. These mechanisms are:

1. Thermal agitation forces, that cause Brownian motion, and are a function of the thermal energy of the system, that is kT, where: k is Boltzmann's constant and T is the absolute temperature.
2. Convective forces, such as shear from fluid flow, a particularly important component of which is the shear rate at the conduit wall expressed as 8V/D for a cylindrical conduit and laminar flow of a Newtonian liquid, where: V is the mean velocity of flow and D is the conduit diameter.
3. The direct effect of temperature on affinity bond formation and bond breaking is a mechanism that plays a significant role and has also been discussed.
4. Cell membrane fluidity as a function of temperature is a mechanism that can impact both affinity site location on the cell surface and mobility of the site within the cell membrane and therefore play a role in affinity bond formation and bond breaking.
5. Forces at the air-liquid interface for occluding air bubbles that can result in a scrubbing effect on the surface of the conduit.

The mechanisms available for placement of cells onto a capture zone are:

1. Gravitational effects (more specifically, sedimentation incorporating gravitational, buoyant, form drag, and friction drag forces)
2. "Fluidic" effects resulting from the differences in shear forces at different locations on the cell surface in laminar flow and in segmented flow.
3. Surface film transport effects in segmented flow with wettable walls.
4. Cell spreading, shape-changing, and new adhesion receptor expression resulting from metabolic activity.
5. Other mechanisms that may be brought about by external means include: laser light pressure, magnetic or electrical fields, etc.
6. Surface chemistry effects resulting, for example, from specialized surface treatment such as the use of non-thrombogenic surface groups (acid polysaccharides, heparin, etc.) and long spacer arms to extend the reach of coupled capture species and the use of positively charged surfaces, as well.
7. Nonspecific binding or adsorption of cells to the surfaces of some materials, presumably due to hydrophobic interactions or other short-range binding forces.

Gravitational effects and fluidic effects in laminar flow are treated in depth in many books and technical articles and will not be discussed here, nor will the other mechanisms, except for the fluidic effects in segmented flow and film transport effects, since these deserve special mention. In the case of a single segment of liquid moving through a conduit (e.g. a cylindrical tube) the flow pattern is far more complicated than that observed in simple laminar flow at similar flow rates. In segmented flow, liquid at the center of the leading edge of the segment moves to the periphery to provide a layer of new liquid on the conduit wall allowing other liquid to subsequently move over it thus advancing the translational position of the liquid segment. If the conduit is not wettable by the liquid, that is if the conduit is a fluorocarbon polymer such as FEP or PTFE and the liquid aqueous, some cells suspended in the liquid will be placed directly on the conduit walls as the segment of liquid advances, since there is no "static" film.

If the conduit material is wettable, that is if the conduit is a material such as PVC or glass and the liquid aqueous, the length of the leading segment of liquid entering dry tubing will be shortened as it loses liquid during its transit. This is because it is laying down a "static" liquid film directly on the conduit wall. After this film is in place, subsequent segments of liquid appear to pass over it. The film thickness is proportional to several variables and was modeled in a slightly different system by Landau and Levich (*Acta Physichim USSR* 17: 42, 1942) as: t=1.34 R[uv/s]2/3, where: t is the film thickness, R the tube radius, u the viscosity of the liquid, v the average velocity of the liquid, and s the liquid-solid surface tension. The film thickness can be varied over a large range, depending upon the materials, conduit radius, and liquids used and the velocity of liquid transport. The range can be from the same order of magnitude as a blood cell to as great as 1 mm or more. In addition, the film is not necessarily static and can be made to flow with a flow rate Q which is modeled in the equation: Q=Ravt, where: R the tube radius, a the slip factor at the air-liquid interface, v the air bolus velocity and d the film thickness. It should also be noted that suspended cells in segmented flow of liquids can tend to concentrate toward the leading or trailing edge of the segment or may become uniformly distributed, depending, in part upon the velocity of flow as well as secondary mixing effects, such as in coiled conduits. In addition, the speeding-up of flow can result in the laying down of a thicker liquid film layer and potentially can transfer greater numbers of cells into this liquid film adjacent to the conduit wall.

There are many factors associated with controlled flow that can influence and direct the transport of cells to the surface of a conduit to achieve efficient capture or controlled delay in transport via affinity binding processes. Precise control of materials, conduit dimensions and pumping are important variables that can be controlled precisely, as has been discussed. The technology described in the present invention advantageously employs these and other factors.

This technology provides a new way to analyze cells that is consistent with their natural surface-mediated functions and in the case of blood cells with their surface-mediated behavior in a flowing stream. The surfaces of blood cells and the endothelial cells that line the blood vessels contain important surface molecules, and the functions of most of these molecules are presently unknown. More than 150 CD (cluster of differentiation) antigens have been identified on these cells, with new ones being discovered all the time. There is a worldwide effort to study CD antigens and even several web sites and databases. The technology described herein can provide direct feedback on cell capture rates to analyze cell capture kinetics mediated by CD antigens. It also affords the possibility of simultaneous analysis of a greater number of surface groups than previously possible. Furthermore, the technology can provide kinetic cell capture feedback to enable computer controlled or modified flow conditions to optimize cell capture. In addition, the cell capture systems described can provide cell concentration information and/or be used in conjunction with cell counting or flow cytometry systems.

FIG. 12 (not to scale) uses a compound microscope 70a, consisting of objective lens 70, field lens 71, and ocular lens 72 to image the cells onto a high resolution digital camera such as a CCD detector array 73 that is connected to camera electronics 74. The camera is connected to computer 76 via video image capture board 75. It should be noted that the objective lens 70 (gathering light rays 67, 68 and 69) can consist of a composite of individual or component lenses as is found, for example, in an immersion achromat of a high quality microscope. The microscope field is moved from capture zone to capture zone by a motion control system, such as a high resolution stepper motor and micrometer drive 70b under the control of computer 76. This motion control system provides motion in the X-Y plane to image all areas of interest and employs two stepper motors and micrometer drives to achieve this under computer control. In addition the motion control system is capable of motion in the Z-direction for automatic focus, using a third stepper motor and drive, also under computer control. In a preferred embodiment, the cartridge containing the capture zones and sample to be tested is moved, and the optics, digital camera, and light sources are maintained in a fixed position. Ideally, the capture zone 24 will take up the entire field of the microscopic image.

A plurality of light sources 65a, 65b, 65c, 65d under control of computer 76 are employed. As illustrated, the light sources provide large angle scatter rays from source 65a, a transmission source from 65b, oblique light from source 65c, and epi-illumination from source 65d in combination with a filter block containing dichroic mirror 65e, excitation filter 65f and emission filter 65g. Each light source may comprise a discreet source of illumination and/or a filter wheel (which filter wheel, if present, is also under control of computer 76, or each light source may be derived from a common source of illumination by means of a fiber optic or a light pipe. As seen in FIG. 12, filter wheel 70c containing filter cubes with dichroic mirrors 65e and 65h, excitation filters 65f and 65i, and emission filters 65g and 65j is driven by shaft 70d connected to stepper motor 70e, which is under control of computer 76. Light source 65d provides epi-illumination via the dichroic mirror 65e, as shown. Suitable sources of illumination include, but are not limited to, xenon flash tubes, laser diodes, lasers, tungsten, or tungsten-halogen sources. By using the computer controller 76 in combination with the control of the light sources and the motion control system, a response file can be produced and stored in the computer for the response, or signature, of the cell or cells as interrogated sequentially under different lighting conditions. By providing at least two light sources (preferably at least transmission illumination and epi-illumination) and preferably a filter wheel in at least one of these light sources, the response file can contain information on the behavior of the corresponding cell under a plurality of different lighting conditions (interrogations).

While it is also advantageous to image only a portion of the capture zone using higher magnification, the important consideration for a system of this type is that each cell can be resolved and size-discriminated by electronic analysis of the image using the computer 76. Cell analysis is achieved by the signature of each cell that is captured. This signature consists of a composite of responses that identify the cell. The discrimination of a captured cell (or a cell capture event) for example is achieved by a light absorption signal from a light source that is activated to provide rays 66. Alternatively, the large angle scatter signal from a light source that is activated to provide rays 65 can be used. A capture event can also be determined from cell discrimination using illumination from an oblique light source that is activated to produce rays 64. With such a source, small angle back scatter information can be preferentially obtained.

An important aspect of the invention is that in addition to measurement of cells that are captured, the system in FIG. 12 can be used to count cells in a given population and to characterize these cells as would a flow cytometer. This is achieved by adding a known volume of sample containing cells, diluting the cells to space them sufficiently so as to avoid coincidence, and settling the cells in a known sample area (somewhat larger than an individual capture zone). The cells are then in the focal plane of the compound microscope objective 70, which is focused on the upper surface of wall 37 of volumetric chamber 28. This chamber is bounded by walls 41 and 37, as shown in FIG. 12. In one embodiment, the cells are mixed with an appropriate microscope stain prior to dilution to help differentiate cell types. The cells can be washed free of excess stain by a variety of means during in vitro preparation, including dialysis, centrifugation, and magnetic bead separation. The cells can then be introduced at the appropriate dilution and measured. Unstained cells can also be measured in the same way, after they have settled on the surface. Cells may be captured and then stained. This may be achieved in a variety of ways, including first capturing the cells, then staining, and subsequently washing out excess stain. Staining can be achieved with cytochemical stains or with surface marker-binding antibody molecules that are coupled to fluorescent label or that become fluorescently labeled via subsequent attachment of a second antibody with fluorescent label, where the second antibody binds to the first antibody. Cell viability stains such as propidium iodide or trypan blue may be similarly used, as well as fluorescent stains for cell cycle determination. The microscope is focused at the upper surface of wall 37, as shown in FIG. 12. As the microscope field moves systematically from section to section along the entire area of the upper surface of chamber wall 37, the number of settled cells is counted. Each cell can be sized by analyzing the number of CCD elements in the array that respond per cell. The position of each cell can also be recorded. For each field of view, a sequential interrogation with each of the light sources is easily achieved and the responses recorded. For example, rays 64 could be emitted by a helium-neon laser, rays 65 and 66a by pulsed xenon sources with borosilicate windows (if UV light is desired) and rays 66 from an infrared LED. This allows quantitative information to be obtained and stored on each cell imaged in the CCD array for each illumination mode. Fiber optic waveguides can also be used, along with filters to pass specific wavelengths. For each illumination geometry, more than one light source or a light source at more than one wavelength can be used sequentially, providing a matrix of response characteristics for each cell. This resulting information is then used to classify cells. Classification variables therefore include size and intensity at each interrogation for each cell and allow a population analysis to be achieved as is typically done in flow cytometry. The principle differences are that the system described analyzes fewer cells per unit time, is less costly, and can provide a different set of cell analysis data in addition to cell capture kinetic data, which flow cytometry cannot provide. Further, the system in FIG. 12 may also be used to measure and analyze the kinetics of agglutination of cells in the presence of cell-cell interactions or the presence of agglutinating antibody or nonspecific agglutinating agents. This is achieved by analyzing the cells in one or more particular fields as a function of time. The cell agglutination reaction may also involve captured cell species.

The system shown in FIG. 12 uses a compound microscope lens and CCD camera to capture the signals of individual cells. An alternative to the use of a CCD camera is to use a flying spot light source (not shown). For example, a focused laser beam spot moving in a raster pattern, or a cathode ray tube as with a television screen, may be used. Light transmitted through (or reflected from) each cell is sent to a photomultiplier tube for detection. Two or more photomultiplier tubes with different optical filters may be employed. The timed sequence of the field sweep and the detected light intensity at each point in time allows the image to be reconstructed and displayed on a video monitor. The use of flying spot or scanning light microscopy is detailed in many books, such as *Modern Microscopy* by V. E. Cosslett, Cornell University Press, Ithaca N.Y., 1966. The scanning may be achieved in a variety of ways, such as with a vibrating mirror. The light beam can also be moved in an up and down vertical line and the subject to be imaged moved in a horizontal motion. For example, a capture zone or guided sedimentation template can be moved at a controlled rate of speed at right angles to the direction of spot movement.

8. Preferred Apparatus and Cartridge

Figure 13:
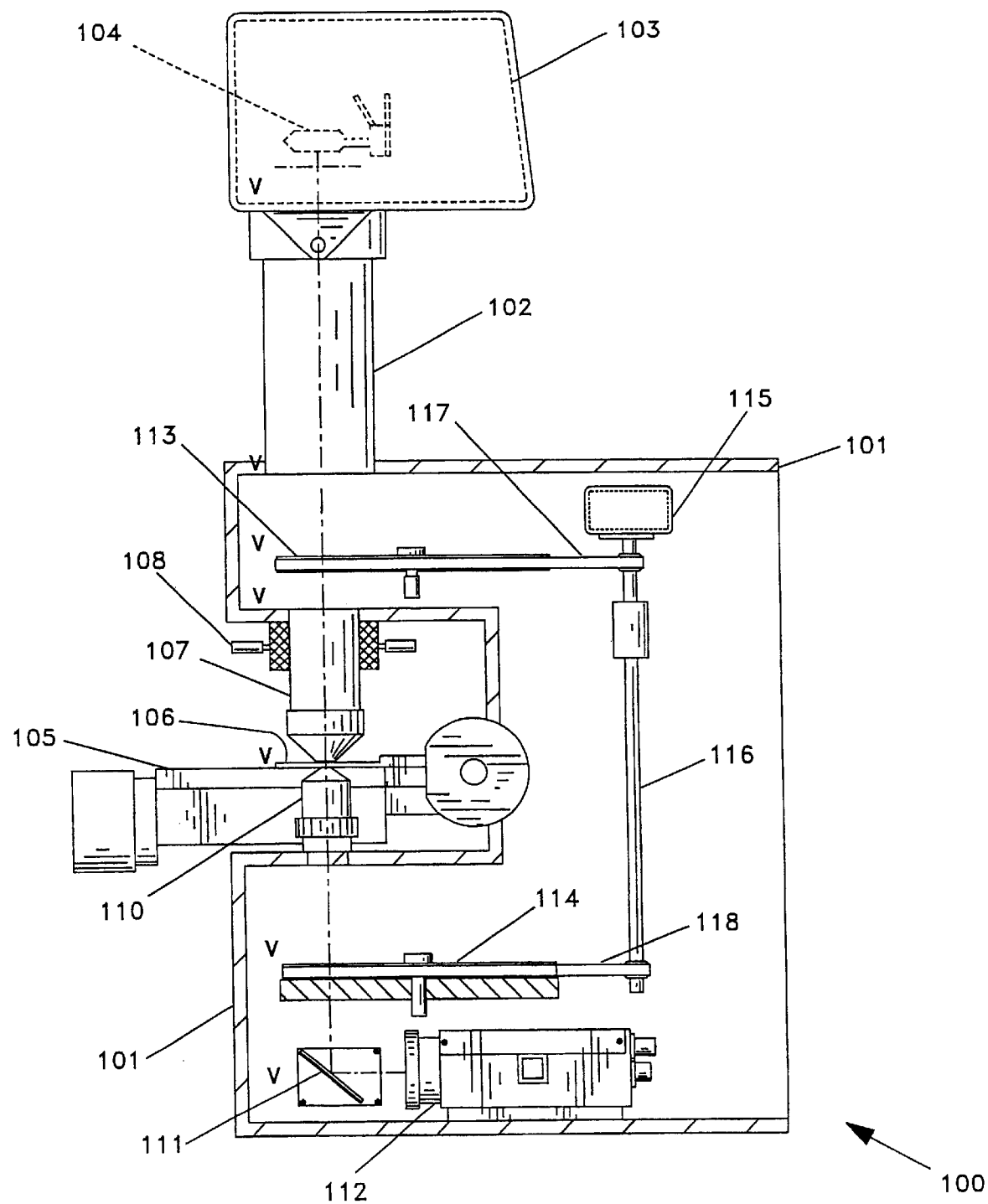
FIG. 13 is a side-sectional view of an apparatus of the invention, showing the arrangement of filters, light source, and light detector.
Figure 14:
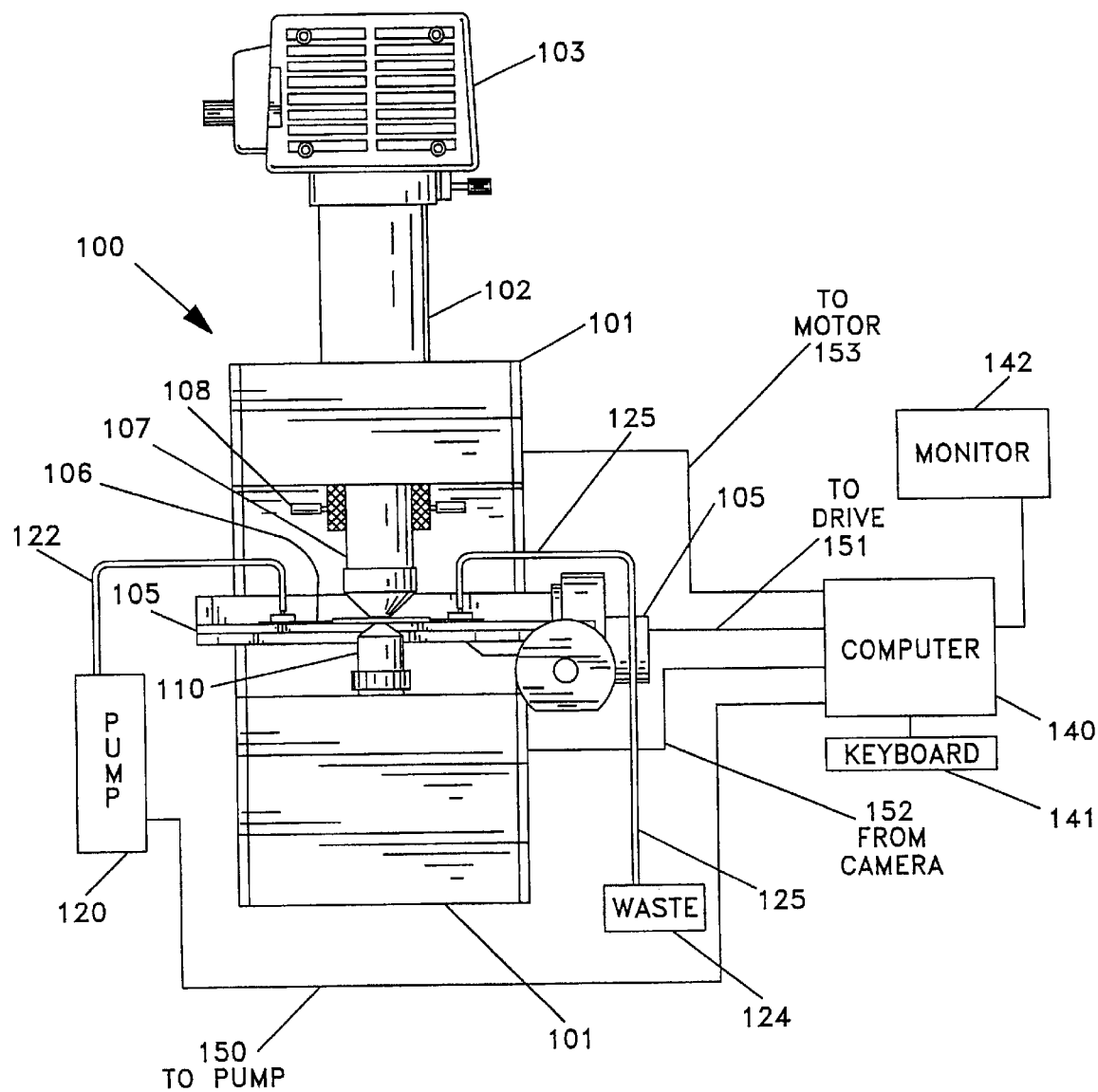
FIG. 14 is a front view of the apparatus of FIG. 13, and also showing the fluid pump and association of a computer controller with the apparatus.

FIGS. 13–14 show one preferred apparatus of the invention. As shown in FIG. 13, the apparatus comprises an imaging unit 100 that includes a body housing 101, a vertical connection tube 102, and light source housing 103 containing a light source 104 (shown in phantom). The light source is preferably Model BH2-HLSH80/100, available from Olympus America Inc. A motorized stage 105 for carrying a cell analysis cartridge 106 is mounted on the body housing. The motorized stage may be an xyz stage, such as Model E5110 available from Prior Scientific Instruments. The light source housing is positioned above and substantially vertically oriented with respect to the motorized stage. A condenser 107 is provided above the motorized stage and secured to the housing by clamp assembly 108. An objective lens 110 is provided below the motorized stage. The objective lens is preferably Model EA40, available from Olympus America Inc. A first surface mirror assembly 111 below the objective lens directs light passing through the condenser and objective lens into the light detector 112, which as illustrated is a CCD camera (preferably a Cohu Model 2122 CCD camera). Different filters are mounted in the excitation filter wheel 113 and the emission filter wheel 114, and the two filter wheels are driven by motor 115 through shaft 116 and belts 117, 118. The motor may be a stepper motor, and is preferably Model 16PY-Q205-T20 available from Minebea Co. Ltd. A preferred set of filters are for direct fluorescence and are available from Chroma Corp as models D480/30X; D535/40M; D540/25X; and D605/55M. The filter wheels could also be driven by separate motors to provide a greater number of combinations of filters.

FIG. 14 schematically illustrates the portions of the apparatus external to the imaging unit 100. A pump 120 is connected to the input port 121 of the cartridge 106 (see FIG. 15) by means of tubing 122, and the outlet port 123 of the cartridge is connected to a waste receptacle 124 by means of tubing 125. The pump is preferably a piston pump or a syringe pump, such as a Cavro Scientific Instruments Model XP300 syringe pump, and is preferably a positive displacement pump. The cartridge 106 includes a top portion 130 and a bottom portion (not shown in FIG. 15; see also FIGS. 16–17, where analogous parts are indicated by an apostrophe and the bottom portion is 131') and a channel formed therebetween, in fluid communication with the inlet and outlet ports. A computer controller 140, typically with a keyboard 141 and monitor 142, is provided to control the method and apparatus. The computer is connected to pump by line 150 through an interface supplied by the pump manufacturer (not shown), and is connected to the motorized stage by line 151 through a control circuit (not shown). The light detector is connected to the computer by line 152. The stepper motor is connected to the computer by line 153 through a control board (not shown). In general, numerous conventional personal computers, outfitted with control circuits or boards, capture boards for connection to the light detector, and running any of a variety of imaging software such as NIH Image Version 1.6.2 (a public domain software) can be employed. Portions may be implemented as described in connection with the Examples below. Control of the drive, filters, and pump is coordinated by software programming and/or hardware in the computer to implement the method steps described herein. For example, one imaging field may be interrogated as described herein, data captured and a response file created, and that field subjected to subsequent interrogation at different wavelengths by control of the filters through the motor, additional data captured and added to the response file, etc. until all interrogations are completed. If desired, then the cartridge may be moved through the stage drive and the interrogation step or steps repeated on a different imaging field.

Figure 15:
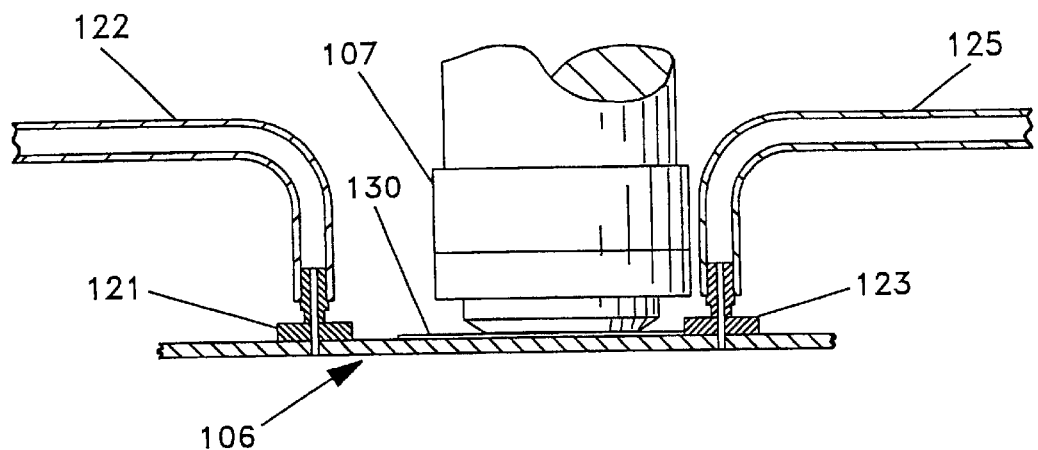
FIG. 15 is a detail view of the apparatus of FIG. 14, showing the problem of limited travel of the condenser over the cartridge due to the vertical orientation of the fluid lines.
Figure 16:
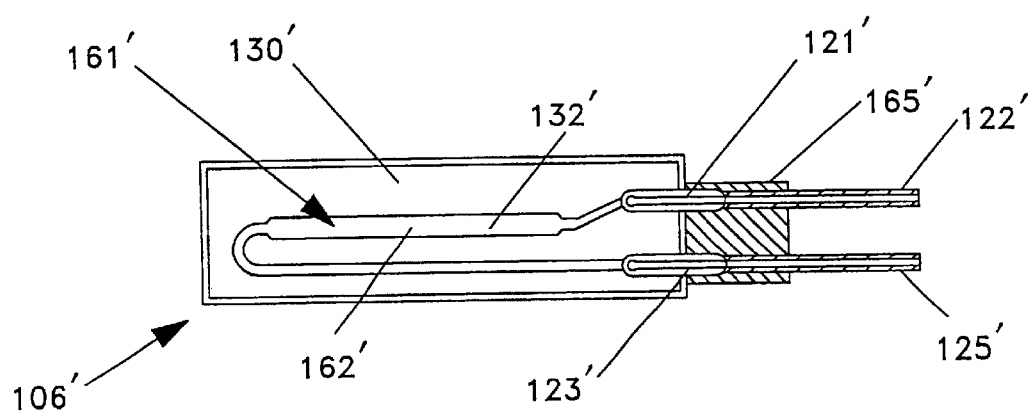
FIG. 16 is a top view of a preferred cartridge for use in the invention, in which inlet and outlet lines are substantially horizontal in orientation, thereby allowing greater range of movement of a condenser over the top portion thereof.
Figure 17:
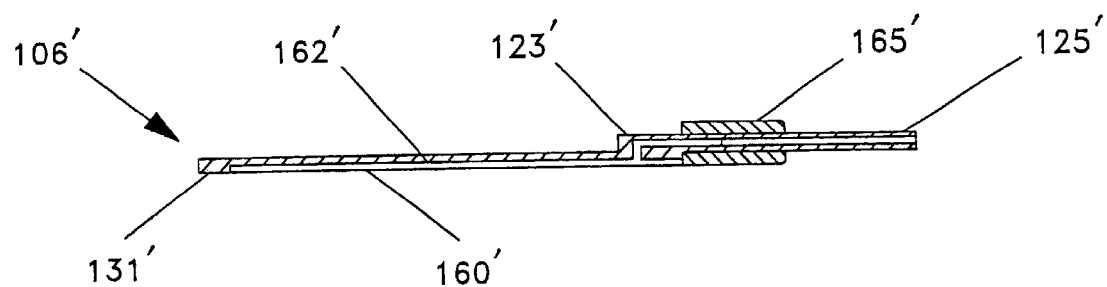
FIG. 17 is a side-sectional view of the cartridge of FIG. 16.

FIG. 15 is a detail view of the apparatus of FIG. 14, showing the problem of limited travel of the condenser over the cartridge due to the vertical orientation of the fluid lines. FIGS. 16–17 show one preferred structure of a cell analysis cartridge for use in the invention, in which inlet and outlet lines are substantially horizontal in orientation, thereby allowing greater range of movement of a condenser over the top portion thereof. In general, the cartridge comprises a substantially flat planar body member 106' having a top portion 130', a bottom portion 131', and an elongate fluid channel 132' formed therein. The cartridge has two openings formed in the body member in fluid communication with the fluid channel, which openings may serve as an inlet and outlet opening 121', 123'. Additional openings, such as additional inlet openings for buffer, wash or stain solutions, etc., may be included if desired. A substantially optically transparent, non-distorting window 160' is formed on either the top or bottom portion, and is formed on the bottom portion of the illustrated embodiment. By "non-distorting" is meant suitable for microscopy at the conditions under which imaging is carried out, consistent with conventional imaging technology. By "substantially optically transparent" is meant that light at the wavelengths necessary to carry out the method passes through the window. Typically, the optically transparent window is also visually transparent. Suitable materials include, but are not limited to, polycarbonate, polystyrene, polybutyrate, polyethylene terephthalate, etc. Depending upon the type of microscopy and illumination carried out (e.g., transmission) it may be desired that the other of the top or bottom portion is also substantially optically transparent, and optionally also visually transparent. An imaging field 161' is formed in the channel and has a cell binding layer 162' formed thereon (e.g., a nonspecific binding layer or a specific binding layer, such as proteins bonded to the surface portion). The imaging field and the cell binding layer may or may not be coextensive with one another. The imaging field is, as illustrated, formed directly on the inner surface of the bottom portion 160', which is formed of a material suitable for providing the window noted above. The inlet and outlet ports are secured to the inlet and outlet lines by means of a stabilizing collar member 165', which may be either press-fit in place, bonded in place with adhesive, integrally formed with the body member, etc. The substantially horizontal orientation of the inlet and outlet ports allows greater movement of the condenser or other optical component about the surface portions of the cartridge, and hence permits a larger imaging field or greater number of separate binding regions and imaging fields, to be incorporated into a smaller cartridge. Note while the inlet and outlet ports are at the same end portion of the cartridge as illustrated, with the fluid channel travelling through the body portion and returning to the same end portion to communicate with both the inlet and outlet ports, the inlet and outlet ports could alternatively be positioned on different ends of the cartridge, or in any other suitable orientation.

9. Settling or Sedimentation Capture

Another embodiment of the invention adapted for cell counting uses an additional principle as the capture means, designated as "guided settling" or "guided sedimentation". In this embodiment, the capture zone has a textured surface that guides cells into discrete locations (e.g., along defined lines) as they settle. Initially, a fixed volume of cells is added to a diluent to spacially separate the cells to provide sufficient space between them so that they will not be coincident upon settling. Numerous textured patterns may be employed. The pattern may be a random pattern, a "sawtooth grate" system for linear guided settling, or an "egg crate" system for point capture of cells on a known x-y coordinate system. Numerous different textured surfaces can be employed, including etched or pitted surfaces in random (including wholly or partially random) patterns, intersecting lines, curved lines, etc. Texturing can be achieved by any of a variety of processes, including etching, micromachining, microlithography, etc. In general, the textured surface will be characterized by a difference between high points and low points within the textured region of from about 2 or 3 to 20 or 30 microns. It is possible to locate the cells along a designated line, groove, point, channel or the like within a textured surface. The use of textured surfaces thus makes it easier to return rapidly to these locations later on, after all of the cells have been examined (with assurance that the cells will still be there) to reexamine cells and/or to remove specific cells for further analysis using micropositioning devices. For use with human blood cells a saw tooth depth or a tooth peak to peak distance of 15 micrometers and 20 micrometers, respectively, typically can be employed. However, depending upon flow velocity and conduit dimensions, the shear forces can vary considerably, necessitating deeper channels in many cases, such that depression depths of at least 30 or even 50 microns may be desirable. If air segments are used, depression depths of 100 or more microns may even be advantageous. Typical substrate materials can vary, depending upon the micromachining processes employed. For example, if photolithography and chemical etching are used, a glass substrate can be employed.

It should be recognized that textured surface capture zones have been described in addition to texture zones that comprise a member of a specific binding pair affixed thereto. The textured surface embodiments are alternatives to flow cytometry systems and may be used in conjunction with systems that have capture zones comprising members of specific binding pairs and therefore analyze cells by affinity binding processes. The combination of these two types of cell capture zones as either multiple discreet zones or as single zones incorporating both a textured surface and affixed members of a specific binding pair can provide a more comprehensive analysis of cells than has previously been achieved. It is also important to recognize that temperature control is an important consideration in these systems, particularly in the affinity-based cell capture systems. It is important to control the temperature, and as has been discussed, intentional variation of the temperature may be used to advantage in cell analysis.

Capture zones used to carry out the present invention may be fenestrated capture zones, i.e., constructed on a fenestrated or microporous substrate. Such a substrate would permit the passage of liquid around captured cells and through the channels or fenestrations formed in the substrate. The opposite or back side of the substrate can be connected to a drain line having a valve positioned therein, the valve under the control of the computer controller to provide a means for controlling, starting and/or stopping of liquid flow through the channels or fenestrations. Fenestrated substrates can be formed from woven or track-etched membranes, polycarbonate, cellulose acetate, polysulfone, micromachined glass, etc. Any suitable means for controlling liquid flow through the channels or fenestrations could be used, such as a manually operated valve. Such fenestrated capture zones are useful for washing cells in situ on the capture zone without subjecting the cells to high shear forces that may be involved in washing the cells by flowing liquid longitudinally through the main channel of the conduit. If a particular material, e.g., fenestrated material, is not transparent, then it should be used along with a transparent material on the opposing surface to allow imaging. It may also be desireable to use reflected light instead of transmitted light to illuminate translucent materials.

10. Universal Capture Zones

A "universal" capture zone can be incorporated into the methods, apparatus and cartridges described herein using first and second specific binding pairs. The first binding specific binding pair may be biotin and avidin; the second specific binding pair may be an antibody or other free binding partner and a cell surface molecule specifically bound by the antibody. One of the biotin or avidin is bound to the substrate surface portion; the other of the biotin or avidin is bound to the free binding partner (e.g., a biotinylated antibody) to form a conjuagate which is added to the carrier solution (or with which the capture zone is pretreated). Other specific binding pairs, such as protein and antibody, can be used in place of the biotin and avidin as the first binding pair. In either case, the selectivity of the binding surface can be modified by changing only the free binding pair in the conjugate. Hence, different cells and different tests may be carried out with the same cartridge or conduit, by changing only the conjugate added to the carrier solution.

The present invention is explained in greater detail in the following nonlimiting examples.

EXAMPLE 1

Live/Dead Cell Assay Protocol With Calcein AM/Ethidium Homodimer 1 (Molecular Probes)

The method was carried out on a conventional fluorescent microscope (Olympus America Model IX50), modified as follows. The light source was an Olympus America Inc Model 5-UL500 light source. The filter sets were Olympus America Inc. HQ480/40; HQ535/50; HQ545/30; and HQ610/75. The cartridge was formed of a top portion, a spacer, and a bottom portion. The top was formed of polycarbonate, particularly LEXAN® polycarbonate sheet available from General Electric. The spacer was formed of Artus Type 119 polymer; The bottom was formed of either Oros Technology polystyrene sheet or K&S Engineering Polybutyrate sheet Type 302, with the parts assembled with 3M corp Type 467MP adhesive. Ports in the cartridge were Cole-Parmer type 6365-30. The pump for providing fluid to the cartridge was a Cavro Scientific Instruments Inc. Model XP300 syringe pump. Any suitable transmission tubing can be used to connect the cartridge to the pump and a receptacle, such as FEP (TEFLON®) tubing supplied by the pump manufacturer. A short length of Helix Medical Silicon Tubing, Part No. 60-011-05, is used as an interface between the transmission tubing and the port. The original camera was a Costar Corp. Model CV235 Camera, connected to a Coreco Model Ultra II 2100 capture board in an Intrex personal computer (200 MHz, MMX Pentium). Imaging software running in the computer for creating the response files is NIH Image Version 1.6.2, available at www.tsc.udel.edu/macsoftdist/image.html.

Basis of Test

Calcein AM is an ester that is transported into the cell and an intracellular esterase cleaves it to a green fluorescent non-transported compound (i.e. it is now trapped inside the cell). Ethidium homodimer 1 only passes through holes in the dead cell membrane (i.e. it can not enter cells possessing intact membranes—live cells) and stains the DNA red.

Reagents

Calcein AM 4 mM in DMSO

Ethidium homodimer 2 mM in DMSO/$H_2O$ (1:4)(v:v)

Saponin 0.6% solution in 0.02% sodium azide (60 mg saponin+10 mL $H_2O$+10 μL 20% $NaN_3$)

100 μM Stock Solutions

Calcein AM

Dil 1:40 (20 μL of 4 mM+780 μL DBSS)

Ethidium homodimer

Dil 1:20 (20 μL of 2 mM+360 μL DBSS)

Calcein AM/Ethidium Homodimer Working Solution

20 μL Calcein AM(100 μM)+50 μL ethidium homodimer (100 μM)+263 μL $H_2O$

Saponin Working Solution

1:8 dilution=10 μL saponin (0.6%)+70 μL $H_2O$

Cell Mixture

25 μL cells

25 μL saponin (1:8 diluted 0.6%)

10 μL Calcein AM/Ethidium homodimer working solution

Procedure

1. Mix cells and saponin
2. Incubate mix at RT for 5 min.
3. Add Calcein AM/ethidium homodimer mix.
4. Incubate at RT for 5 min.
5. Count green (live) using 480 nm excitation and 535 nm emission filters and count red (dead) cells using 540 nm excitation and 605 nm emission filters.

EXAMPLE 2

Capture and Propidium Iodide Staining of Human White Blood Cells

This example is carried out with human white blood cells in a cartridge-type apparatus as described in Example 1 above, in accordance with the specific procedures set forth below.

Preparation of Washed Buffy Coat Cells

Draw 100 μL of human blood into a heparinized capillary tube

Centrifuge blood-filled capillary at 1000×g for 10 minutes

Break capillary tube just below the erythrocyte/white cell interface

Discard erythrocyte fraction

Expel the white cells/plasma fraction into 500 μL of DBSS wash solution

Centrifuge cells at 750×g for 5 minutes

Decant wash solution

Repeat wash step

Suspend washed cells in 100 μL DBSS (Delbecco's Phosphate Buffered Saline)

White Cell Capture

Assemble cartridge with polybutyrate capture surface

Fill cartridge with suspended/washed white cell preparation

Allow cells to settle for 10 minutes

Connect pump to cartridge

Wash cell channel at controlled flow rate until most erthrocytes are washed away Saponin/Propidium Iodide Treatment Fill cartridge with 0.05% saponin in DBSS containing 50 μg propidium iodide Incubate cell-filled cartridge at room temperature for 5 minutes Detection of "Stained" Cells Using filter block with 535 nm excitation and 617 nm emission characteristics, quantitate "red" glowing cells.

The foregoing is illustrative of the present invention, and is not to be construed as limiting thereof. The invention is defined by the following claims, with equivalents of the claims to be included therein.

What is claimed is:

1. A method of analyzing cells in a carrier solution, comprising:

(a) introducing said carrier solution into a conduit having a surface portion wherein the surface portion has a discreet capture zone formed therein, said carrier solution having a plurality of cells suspended therein;

(b) contacting said plurality of said cells to said surface portion, said surface portion containing at least one imaging field;

(c) sequentially interrogating said plurality of cells in said imaging field with at least two different types of emitted light;

(d) processing resultant light from said imaging field for each of said at least two different types of emitted light;

(e) generating digital information for each of said plurality of cells from said resultant light for each of said at least two different types of emitted light; and then (f) generating a response file for each of said plurality of cells from said digital information for each of said at least two different types of emitted light;

and wherein said sequentially interrogating step is followed by the steps of: altering the temperature of said cells in said capture zone; and then repeating said sequentially interrogating step.

2. The method according to claim 1, wherein said introducing step is carried out by flowing said solution through said conduit.

3. The method according to claim 1, wherein said contacting step is carried out by allowing said cells to settle on said surface portion.

4. The method according to claim 1, wherein said surface portion has a first discrete capture zone formed thereon, with said capture zone positioned in said imaging field, and wherein said contacting step is carried out by binding said cells to said first capture zone.

5. The method according to claim 1, wherein said at least two different types of emitted light differ in a property selected from the group consisting of frequency, intensity, direction of travel with respect to said cells, and combinations thereof.

6. The method according to claim 1, wherein said resultant light is selected from the group consisting of light reflected by, absorbed by, scattered by, transmitted through, generated by molecules associated with said cells, and generated by molecules displaced by said cells.

7. The method according to claim 1, wherein said carrier solution comprises a biological fluid or buffered sample medium.

8. The method according to claim 1, wherein said surface portion is a flat surface portion.

9. The method according to claim 1, wherein said processing step comprises an optical detection step followed by an electronic processing step.

10. The method according to claim 1, wherein said response file includes the location and boundaries of each of said plurality of cells.

11. The method according to claim 1, further comprising staining said cells following said contacting step.

12. The method according to claim 1, further comprising generating a histogram plot of parameters for said plurality of cells from said response files.

13. The method according to claim 1, further comprising generating a cell scatter or cell distribution diagram from said response files.

14. The method according to claim 1, further comprising determining viability for each of said plurality of cells from said response files.

15. The method according to claim 1, further comprising determining the proliferation index of said plurality of cells from said response files.

16. The method according to claim 1, further comprising determining the incidence of apoptosis of said cells from said response files.

17. The method according to claim 1, further comprising counting said cells from said response files.

18. The method according to claim 1, further comprising determining the DNA content of said cells from said response files.

19. The method according to claim 1, further comprising detecting specific cytoplasmic or cell surface markers from said response files.

20. The method according to claim 1, further comprising determining the activation state of said cells from said response files.

21. The method according to claim 1, further comprising classifying said plurality of cells according to type from said response files.

22. The method according to claim 1, wherein said cells are live cells.

23. The method according to claim 4, said surface portion having at least a second discrete capture zone formed thereon to provide a plurality of different discrete capture zones, each positioned in an imaging field;

and wherein said sequentially interrogating step is repeated for each of said discrete capture zones.

24. The method according to claim 4, wherein said cells are blood cells, and wherein said blood cells bind to said capture zone.

25. The method according to claim 1, wherein the flow of said cells in said solution during said contacting step is modified by feedback from said resultant light or said response files.

26. The method according to claim 1, wherein said sequentially interrogating step is followed by altering the rate of flow of said solution through said conduit; and then repeating said sequentially interrogating step.

27. The method according to claim 1, further comprising lysing cells bound to said capture zone, and then analyzing nucleic acid released from said lysed cells;

and wherein said lysing follows said contacting step.

28. The method according to claim 1, further comprising transiently permeabilizing said cells to release a portion of the contents thereof, while retaining nucleic acid for subsequent analysis therein;

and wherein said cells are transiently permeabilized after said contacting step.

29. The method according to claim 4, wherein said capture zone comprises an affinity species immobilized on said surface portion.

30. The method according to claim 4, wherein said capture zone comprises a textured segment of said surface portion.

31. The method according to claim 1, further comprising permeabilizing cells bound to said first capture zone;

and wherein said permeabilizing step follows said contacting step.

* * * * *